United States Patent [19]

Doherty et al.

[11] Patent Number: 5,663,296
[45] Date of Patent: Sep. 2, 1997

[54] HYDROXAMATE INHIBITORS OF ENDOTHELIN CONVERTING ENZYME

[75] Inventors: Annette Marian Doherty; Brian Edward Kornberg; Sham Nikam, all of Ann Arbor, Mich.

[73] Assignee: Warner-Lambert Company, Morris Plains, N.J.

[21] Appl. No.: 373,911

[22] Filed: Jan. 17, 1995

Related U.S. Application Data

[63] Continuation of Ser. No. 70,161, May 28, 1993, abandoned.
[51] Int. Cl.$^6$ ................................................. A61K 38/06
[52] U.S. Cl. ................................... 530/331; 548/496
[58] Field of Search .......................... 514/18, 17, 19; 530/331; 548/496

[56] References Cited

FOREIGN PATENT DOCUMENTS

| | | |
|---|---|---|
| 0345359 | 12/1989 | European Pat. Off. ........ C07K 5/10 |
| 376040A2 | 7/1990 | European Pat. Off. . |
| 410411A2 | 1/1991 | European Pat. Off. . |
| 0518299 | 12/1992 | European Pat. Off. . |
| 9013561 | 11/1990 | WIPO . |
| 9213944 | 8/1992 | WIPO . |
| 9213545 | 8/1992 | WIPO . |
| 9311154 | 6/1993 | WIPO . |

OTHER PUBLICATIONS

International Search Report—Corresponding PCT Application PCT/US94/05888 Mailed Oct. 4, 1994.

European Journal of Biochemistry, vol. 150, No.1, Jul. 1985, pp. 135–140.

Molecular Pharmacology, vol. 30, No. 4, Oct. 1986, pp. 338–344.

M. Fujino, et al., "Highly Potent Analogues of Enkephalin" *Peptide Chemistry* 1979, pp. 205–208.

Biorganic & Medicinal Chemistry Letters, vol. 2, No. 12, 1992, GB, pp. 1685–1690.

Chen, *Bioorg Med Chem Lett* 2, 1685, 1992.

Abstract 89–210052/29 JO 1146–896–A Fuji Pharm Ind KK FUJY Apr. 12, 1987.

*Primary Examiner*—Cecilia J. Tsang
*Assistant Examiner*—David Lukton
*Attorney, Agent, or Firm*—Francis J. Tinney

[57] ABSTRACT

Hydroxamate compounds of the following formula are disclosed:

$$R-AA^3-AA^4-AA^5-AA^6-NH-OR^2$$

wherein $AA^3-AA^6$ represent amino acid residues. The disclosed compounds are inhibitors of endothelin converting enzyme, and as such are useful for the treatment of disorders resulting from overproduction of endothelin, i.e., acute and chronic renal failure, cyclosporin-A induced nephrotoxicity, hypertension, myocardial infarction, metabolic, endocrinological, neurological disorders, congestive heart failure, endotoxic shock and hemorrhagic shock, septic shock, subarachnoid hemorrhage, arrhythmias, asthma, preeclampsia, atherosclerotic disorders including Raynaud's disease, cerebral vasospasm, restenosis, angina, cancer, pulmonary hypertension, ischemic disease, gastric mucosal damage, ischemic bowel disease, and diabetes.

11 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
        Xaa  Xaa  Xaa  Xaa  Xaa
        1                    5
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
        Xaa  Xaa  Xaa  Xaa  Xaa  Xaa  Xaa
        1                    5
```

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
        Xaa  Ile  Ile  Trp
        1
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
        Asp  Ile  Ile  Trp
        1
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
        Xaa  Asp  Ile  Ile  Trp
        1                    5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
        Leu  Asp  Ile  Ile  Trp
        1                    5
```

-continued ( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Xaa  Leu  Asp  Ile  Ile  Trp
        1                      5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

His  Leu  Asp  Ile  Ile  Trp
        1                      5

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Xaa  His  Leu  Asp  Ile  Ile  Trp
        1                      5

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Xaa  Ile  Ile  Phe
        1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Xaa  Ile  Ile  Xaa
        1

( 2 ) INFORMATION FOR SEQ ID NO:12:

( i ) SEQUENCE CHARACTERISTICS:
        ( A ) LENGTH: 4 amino acids
        ( B ) TYPE: amino acid (D) TOPOLOGY: linear (ii) MOLECULE TYPE: peptide (xi) SEQUENCE DESCRIPTION: SEQ ID NO:12:

Asp Ile Ile Phe
1

(2) INFORMATION FOR SEQ ID NO:13:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:13:

Xaa Asp Ile Ile Phe
1               5

(2) INFORMATION FOR SEQ ID NO:14:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:14:

Asp Ile Ile Xaa
1

(2) INFORMATION FOR SEQ ID NO:15:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:15:

Xaa Asp Ile Ile Xaa
1               5

(2) INFORMATION FOR SEQ ID NO:16:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:16:

Xaa Xaa Xaa Xaa Xaa Xaa
1               5

HYDROXAMATE INHIBITORS OF ENDOTHELIN CONVERTING ENZYME

This application is a continuation of Ser. No. 08/070,161, filed May 28, 1993, now abandoned.

BACKGROUND OF THE INVENTION

The present invention relates to novel hydroxamate inhibitors of endothelin converting enzyme useful as pharmaceutical agents, to methods for their production, to pharmaceutical compositions which include these compounds and a pharmaceutically acceptable carrier, and to pharmaceutical methods of treatment. More particularly, the novel compounds of the present invention are inhibitors of endothelin converting enzyme useful in treating elevated levels of endothelin and in controlling hypertension, myocardial infarction, metabolic, endocrinological, and neurological disorders, congestive heart failure, endotoxic and hemorrhagic shock, septic shock, subarachnoid hemorrhage, arrhythmias, asthma, acute and chronic renal failure, cyclosporin-A induced nephrotoxicity, restenosis, angina, ischemic disease, gastric mucosal damage, ischemic bowel disease, cancer, pulmonary hypertension, preeclampsia, atherosclerotic disorders including Raynaud's disease, cerebral vasospasm, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogs with incorrect disulfide pairings exhibit at least 100-fold less vasoconstrictor activity.

Endothelin-1 is generated from a 203 amino acid peptide known as preproendothelin by an unknown dibasic endopeptidase. This enzyme cleaves the prepropeptide to a 38 (human) or 39 (porcine) amino acid peptide known as big endothelin or proendothelin. Big ET is then cleaved by an enzyme, known as endothelin converting enzyme or ECE, to afford the biologically active molecule ET-1. Big ET is only 1% as potent as ET-1 in inducing contractile activity in vascular strips but it is equally potent in vivo at raising blood pressure, presumably by rapid conversion to ET-1 (Kimura S, Kasuya Y, Sawamura T, et al, "Conversion of big endothelin-1 to 21-residue endothelin-1 is essential for expression of full vasoconstrictor activity: Structure-activity relationship of big endothelin-1," *J. Cardiovasc Pharmacol* 1989;13:S5). There have been numerous reports describing possible proteases in both the cytoplasm and membrane bound cellular fractions of endothelial cells (Ikegawa R, Matsumura Y, Takaoka M, et al, "Evidence for pepstatin-sensitive conversion of porcine big endothelin-1 to endothelin-1 by the endothelial cell extract," *Biochem Biophys Res Commun* 1990;167:860; Sawamura T, Kimura S, Shinmi O, et al, "Characterization of endothelin converting enzyme activities in soluble fraction of bovine cultured endothelial cells," *Biochem Biophys Res Commun* 1990;169:1138; Sawamura T, Shinmi O, Kishi N, et al, "Analysis of big endothelin-1 digestion by cathepsin D," *Biochem Biophys Res Commun* 1990;172:883; Shields P P, Gonzales T A, Charles D, et al, "Accumulation of pepstatin in cultured endothelial cells and its effect on endothelin processing," *Biochem Biophys Res Commun* 1991;177:1006; Matsumura Y, Ikegawa R, Tsukahara Y, et al, "Conversion of big endothelin-1 to endothelin-1 by two types of metalloproteinases derived from porcine aortic endothelial cells," *FEBS Lett*, 1990;272:166; Sawamura T, Kasuya Y, Matsushita S N, et al, "Phosphoramidon inhibits the intracellular conversion of big endothelin-1 to endothelin-1 in cultured endothelial cells," *Biochem Biophys Res Commun* 1991;174:779; Takada J, Okada K, Ikenaga T, et al, "Phosphoramidon-sensitive endothelin-converting enzyme in the cytosol of cultured bovine endothelial cells," *Biochem Biophys Res Commun* 1991;176:860; Ahn K, Beningo K, Olds G, Hupe D, "Endothelin-converting enzyme from bovine and human endothelial cells," *J Vasc Res* 1991;29:76, 2nd International symposium on endothelium-derived vasoactive factors). Many groups have chosen to isolate ECE from endothelial cells of various species, since endothelin is known to be synthesized and secreted by this cell type. It was initially reported that two types of protease activity were present in porcine or bovine endothelial cells that could cause conversion of big ET to ET in vitro (Ikegawa R, supra; Sawamura T, supra; Matsumura Y, supra; Takada J, supra; Ahn K, supra). However, it was subsequently found that the aspartic protease activity from porcine endothelial cells, thought to be predominantly cathepsin D, also caused further degradation of ET-1 and was therefore unlikely to be the true ECE (Sawamura T, supra). Moreover, human cathepsin D also causes rapid degradation of ET-1. In addition, there has been one study showing that the intracellular accumulation of pepstatin, an aspartic protease inhibitor, did not inhibit ET-1 production in cultured bovine aortic endothelial cells (Shields P P, supra). Stronger evidence that ECE is in fact a neutral metalloprotease has appeared (Matsumura Y, supra; Sawamura T, supra; Takada J, supra; Ahn K, supra), although to date there have been no known specific metalloprotease ECE inhibitors to confirm these findings in vivo. However, the nonspecific metalloproteinase inhibitor, phosphoramidon, has been shown to inhibit the intracellular conversion of big ET-1 to ET-1 in cultured vascular endothelial cells and smooth muscle cells (Sawamura T, supra).

ET-converting activity has been detected in both the membranous and cytosolic fractions of cultured porcine, bovine, and human endothelial cells (Matsumura Y, supra). Micromolar concentrations of phosphoramidon have been shown to block the pressor response of big ET both in vitro and in vivo (Takada J, supra; Fukuroda T, Noguchi K, Tsuchida S, et al, "Inhibition of biological actions of big endothelin-1 by phosphoramidon," *Biochem Biophys Res Commun* 1990;172:390; Matsumura Y, Hisaki K, Takaoka M, Morimoto S, "Phosphoramidon, a metalloproteinase inhibitor, suppresses the hypertensive effect of big endothelin-1," *Eur J Pharmacol* 1990;185:103; McMahon E G, Palomo M A, Moore W M, et al, "Phosphoramidon blocks the pressor activity of porcine big endothelin-1-(1–39) in vivo and conversion of big endothelin-1-(1–39) to endothelin-1-(1–21) in vitro," *Proc Natl Acad Sci USA* 1991;88:703). It has recently been reported that phosphoramidon is able to inhibit vasoconstrictor effects evoked by intravenous injections of big ET-1 in anaesthetized pigs, but did not have any effect on the plasma ET-1 level (Modin A, Pernow J, Lundberg J M, "Phosphoramidon inhibits the vasoconstrictor effects evoked by big endothelin-1 but not the elevation of plasma endothelin-1 in vivo," *Life Sci* 1991;49:1619). It should be noted that phosphoramidon is a rather general metalloproteinase inhibitor and clearly the discovery of specific ECE inhibitors such as those described in the present invention is important.

Endothelin is involved in many human disease states.

Several in vivo studies with ET antibodies have been reported in disease models. Left coronary artery ligation and reperfusion to induce myocardial infarction in the rat heart, caused a four- to seven-fold increase in endogenous endothelin levels. Administration of ET antibody was reported to reduce the size of the infarction in a dose-dependent manner (Watanabe T, et al, "Endothelin in Myocardial Infarction," *Nature* (Lond.) 1990;344:114). Thus, ET may be involved in the pathogenesis of congestire heart failure and myocardial ischemia (Marguiles K B, et al, "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon V, et al, "Glomerular Actions of Endothelin In Vivo," *J Clin Invest* 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N, et al, "Endothelin Mediates the Renal Vasoconstriction Induced by Cyclosporine in the Rat," *J Am Soc Nephrol* 1990;1:76).

Others have reported inhibition of ET-1 or ET-2-induced vasoconstriction in rat isolated thoracic aorta using a monoclonal antibody to ET-1 (Koshi T, et al, "Inhibition of Endothelin (ET)-1 and ET-2-Induced Vasoconstriction by Anti-ET-1 Monoclonal Antibody," *Chem Pharm Bull* 1991;39:1295).

Combined administration of ET-1 and ET-1 antibody to rabbits showed significant inhibition of the blood pressure and renal blood flow responses (Miyamori I, et al, Systemic and Regional Effects of Endothelin in Rabbits: Effects of Endothelin Antibody," *Clin Exp Pharmacol Physiol* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY), there were no significant changes in these parameters (Ohno A, "Effects of Endothelin-Specific Antibodies and Endothelin in Spontaneously Hypertensive Rats," *J Tokyo Women's Med Coll* 1991;61:951).

In addition, elevated levels of endothelin have been reported in several disease states (see Table I below).

TABLE I

Plasma Concentrations of ET-1 in Humans

| Condition | Normal Condition | ET Plasma Levels Reported (pg/mL) |
|---|---|---|
| Atherosclerosis | 1.4 | 3.1 pmol/L |
| Surgical operation | 1.5 | 7.3 |
| Buerger's disease | 1.6 | 4.8 |

TABLE I-continued

Plasma Concentrations of ET-1 in Humans

| Condition | Normal Condition | ET Plasma Levels Reported (pg/mL) |
|---|---|---|
| Takayasu's arteries | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction (several reports) | 1.5 | 3.3 |
| | 6.0 | 11.0 |
| | 0.76 | 4.95 |
| | 0.50 | 3.8 |
| Subarachnoid hemorrhage | 0.4 | 2.2 |
| Crohn's disease | 0–24 Fmol/mg | 4–64 Fmol/mg |
| Ulcerative colitis | 0–24 Fmol/mg | 20–50 Fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis (several reports) | <7 | 10.9 |
| | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 (after removal) | 16.2 |

Burnett and co-workers recently demonstrated that exogenous infusion of ET (2.5 ng/kg/mL) to anesthetized dogs, producing a doubling of the circulating concentration, did have biological actions (Lerman A, et al, "Endothelin Has Biological Actions at Pathophysiological Concentrations," *Circulation* 1991;83:1808). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to three-fold elevation of circulating ET levels has been reported (Cavero P G, et al, "Endothelin in Experimental Congestive Heart Failure in the Anesthetized Dog," *Am J Physiol* 1990;259:F312), and studies in humans have shown similar increases (Rodeheffer R J, et al, "Circulating Plasma Endothelin Correlates With the Severity of Congestire Heart Failure in Humans," *Am J Hypertension* 1991;4:9A). When ET was chronically infused into male rats, to determine whether a long-term increase in circulating ET levels would cause a sustained elevation in mean arterial blood pressure, significant, sustained, and dose-dependent increases in mean arterial blood pressure were observed. Similar results were observed with ET-3 although larger doses were required (Mortenson L H, et al, "Chronic Hypertension Produced by Infusion of Endothelin in Rats," *Hypertension* 1990;15:729). Recently the nonpeptide endothelin antagonist RO 46-2005 has been reported to be effective in models of acute renal ischemia and subarachnoid hemorrhage in rats (3rd International Conference on Endothelin, Houston, Tex., February 1993). In addition, the $ET_A$ antagonist BQ-153 has also been shown to prevent early cerebral vasospasm following subarachnoid hemorrhage after intracisternal injection (Clozel M, et al, *Life Sciences*

1993;52:825); to prevent blood pressure increases in stroke-prone spontaneously hypertensive rats (Nishikibe M, et al, *Life Sciences* 1993;52:717); and to attenuate the renal vascular effects of ET-1 in anaesthetized pigs (Cirino M, et al, *J Pharm Pharmacol* 1992;44:782).

The distribution of the two cloned receptor subtypes, termed $ET_A$ and $ET_B$, have been studied extensively (Arai H, et al, *Nature* 1990;348:730; Sakurai T, et al, *Nature* 1990;348:732). The $ET_A$, or vascular smooth muscle receptor, is widely distributed in cardiovascular tissues and in certain regions of the brain (Lin HY, et al, *Proc Natl Acad Sci* 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A, et al, *Biochem Biophys Res Chem* 1991;178:656; Hosoda K, et al, *FEBS Lett* 1991;287:23). The $ET_A$ receptor clearly mediates vasoconstriction and there have been a few reports implicating the $ET_B$ receptor in the initial vasodilatory response to ET (Takayanagi R, et al, *FEBS Lett* 1991;282:103). However, recent data has shown that the $ET_B$ receptor can also mediate vasoconstriction in some tissue beds (Panek R L, et al, *Biochem Biophys Res Commun* 1992;183(2):566).

Plasma endothelin-1 levels were dramatically increased in a patient with malignant hemangio-endothelioma (Nakagawa K, et al, *Nippon Hifuka Gakkai Zasshi* 1990;100:1453).

The ET receptor antagonist BQ-123 has been shown to block ET-1-induced bronchoconstriction and tracheal smooth muscle contraction in allergic sheep providing evidence for expected efficacy in bronchopulmonary diseases such as asthma (Noguchi, et al, *Am Rev Respir Dis* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B A, et al, *Am J Obstet Gynecol* 1992;166:962).

Plasma immunoreactive endothelin-1 concentrations are elevated in patients with sepsis and correlate with the degree of illness and depression of cardiac output (Pittett J, et al, *Ann Surg* 1991;213(3):261).

In addition, the ET-1 antagonist BQ-123 has been evaluated in a mouse model of endotoxic shock. This $ET_A$ antagonist significantly increased the survival rate in this model (Toshiaki M, et al, 20.12.90. EP 0 436 189 A1).

Endothelin is a potent agonist in the liver eliciting both sustained vasoconstriction of the hepatic vasculature and a significant increase in hepatic glucose output (Gandhi C B, et al, *J of Biolog Chem* 1990;265(29):17432).In streptozotocin-diabetic rats, there is an increased sensitivity to endothelin-1 (Tammesild P J, et al, *Clin Exp Pharmacol Physiol* 1992;19(4):261). In addition, increased levels of plasma ET-1 have been observed in microalbuminuric insulin-dependent diabetes mellitus patients indicating a role for ET in endocrine disorders such as diabetes (Collier A, et al, *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M K, et al, *J Hypertension* 1992;10(Suppl 4):S49). The endothelins have been shown to be arrhythmogenic, and to have positive chronotropic and inotropic effects, thus ET receptor blockade would be expected to be useful in arrhythmia and other cardiovascular disorders (Hah S-P, et al, *Life Sci* 1990;46:767).

The widespread localization of the endothelins and their receptors in the central nervous system and cerebrovascular circulation has been described (Nikolov R K, et al, *Drugs of Today* 1992;28(5):303). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, ie, in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1-induced lesion development in a new model of local ischemia in the brain has been described.

Circulating and tissue endothelin immunoreactivity is increased more than two-fold in patients with advanced atherosclerosis (Lerman A, et al, *New England J Med* 1991;325:997). Increased endothelin immunoreactivity has also been associated with Buerger's disease (Kanno K, et al, *J Amer Med Assoc* 1990;264 2868) and Raynaud's phenomenon (Zamora M R, et al, *Lancet* 1990;336:1144). Likewise, increased endothelin concentrations were observed in hypercholesterolemic rats (Horio T, et al, *Atherosclerosis* 1991;89:239).

An increase of circulating endothelin levels was observed in patients that underwent percutaneous transluminal coronary angioplasty (PTCA) (Tahara A, et al, *Metab Clin Exp* 1991;40:1235; Sanjay K, et al, *Circulation* 1991;84(Suppl. 4):726).

Increased plasma levels of endothelin have been measured in rats (Stelzner T J, et al, *Am J Physiol* 1992;262:L614) and humans (Miyauchi T, et al, *Jpn J Pharmacol* 1992;58:279P; Stewart D J, et al, *Ann Internal Medicine* 1991;114:464) with pulmonary hypertension.

Elevated levels of endothelin have also been measured in patients suffering from ischemic heart disease (Yasuda M, et al, *Amer Heart J* 1990;119:801; Ray S G, et al, *Br Heart J* 1992;67:383) and either stable or Unstable angina (Stewart J T, et al, *Br Heart J* 1991;66:7).

Infusion of an endothelin antibody 1 hour prior to and 1 hour after a 60-minute period of renal ischaemia resulted in changes in renal function versus control. In addition, an increase in glomerular platelet-activating factor was attributed to endothelin (Lopez-Farre A, et al, *J Physiology* 1991;444:513-). In patients with chronic renal failure as well as in patients on regular hemodialysis treatment mean plasma endothelin levels were significantly increased (Stockenhuber F, et al, *Clin Sci* (Lond.) 1992;82:255). In addition, it has been suggested that the proliferative effect of endothelin on mesangial cells may be a contributing factor in chronic renal failure (Schultz P J, *J Lab Clin Med* 1992;119:448).

Local intra-arterial administration of endothelin has been shown to induce small intestinal mucosal damage in rats in a dose-dependent manner (Mirua S, et al, *Digestion* 1991;48:163). Administration of endothelin-1 in the range of 50–500 pmol/kg into the left gastric artery increased the tissue type plasminogen activator release and platelet activating formation and induced gastric mucosal hemorrhagic change in a dose-dependent manner (Kurose I, et al, *Gut* 1992;33:868). Furthermore, it has been shown that an anti-ET-1 antibody reduced ethanol-induced vasoconstriction in a concentration-dependent manner (Masuda E, et al, *Am J Physiol* 1992;262:G785). Elevated endothelin levels have been observed in patients suffering from Crohn's disease and ulcerative coliris (Murch S R, et al, *Lancet* 1992;339:381).

Japanese Published Patent Application JP 04041430-A, published Feb. 12, 1992, disclosed phosphoramidon as an endothelin converting enzyme inhibitor.

PCT International Published Patent Application WO 92/12170, published Jul. 23, 1992, discloses peptides of up to 20 amino acids including pentapeptides of the formula:

$$A_3-A_4-A_5-A_4^1-A_3^1 \quad \text{(SEQ ID NO: 1)}$$

wherein $A_3$ and $A_3^1$ independently represent Ser, Gly, Asp, or Asn and $A_4$ and $A_4^1$ independently represent Val, Pro, Gly, or Ala and $A_5$ represents Asp or Asn. The peptides are disclosed to be inhibitors of endothelin formation.

PCT International Published Patent Application WO 92/01468, published Feb. 16, 1992, discloses compounds of the formula:

$$X-\overset{\overset{O}{\|}}{\underset{\underset{OH}{|}}{P}}-A_1-A_2-R_1$$

wherein $A_1$, $A_2$ is an amino acid;
X is OH or a monosaccharide residue;
$R_1$ is OH, alkyl, alkoxy, allyl, or $NR_2R_3$,
wherein $R_2$, $R_3$ is H or alkyl.

The compounds are disclosed as agents for inhibiting endothelin converting enzyme.

PCT International Published Patent Application WO 92/13545, published Aug. 20, 1992, discloses compounds of the formula (these compounds also are described in Shiosaki K, et al, *Journal of Medicinal Chemistry* 1993;36:468):

$$A-B-C-NH\underset{OH}{\overset{R}{\diagdown}}X\diagdown D-E \quad (I)$$

wherein A is hydrogen, an N-protecting group or $R_1NHCH(R_2)C(O)$— wherein $R_1$ is H or an N-protecting group and $R_2$ is hydrogen, lower alkyl, cycloalkyl, cycloalkylalkyl, carboxyalkyl, or alkoxycarbonylalkyl; or A is $HO_2C(CH_2)_nC(O)$— wherein n is one to 3;

B is —$N(R_4)CH(R_3)C(O)$— wherein $R_4$ is hydrogen or lower alkyl and $R_3$ is lower alkyl, cycloalkyl, or cycloalkylalkyl;

C is —$N(R_5)CH(R_6)C(O)$— wherein $R_5$ is hydrogen or lower alkyl and $R_6$ is hydrogen, lower alkyl, cycloalkyl, or cycloalkylalkyl;

R is lower alkyl, cycloalkyl, cycloalkylalkyl, aryl, or bicyclic heterocyclic;

X is —$CH_2$— or —$C(O)$—;

D is (1) —$OR_7$ wherein $R_7$ is hydrogen, lower alkyl, cycloalkyl, or cycloalkylalkyl;

(2) —$NR_8R_9$ wherein $R_8$ and $R_9$ are independently selected from hydrogen, lower alkyl, cycloalkyl, cycloalkylalkyl, and —$(CH_2)_m$—Z wherein m is two to eight and Z is —OH, heterocyclic, —$SO_3H$, —$CO_2R_{10}$ wherein $R_{10}$ is hydrogen or lower alkyl or Z is —$NR_{11}R_{12}$ wherein $R_{11}$ and $R_{12}$ are independently selected from hydrogen, lower alkyl, cycloalkyl, and cycloalkylalkyl;

(3) —$NHCH(R_{13})C(O)$— wherein $R_{13}$ is hydrogen, lower alkyl, cycloalkyl, or cycloalkylalkyl; or (4) —$NHCH(R_{13})C(O)NHCH(R_{14})C(O)$— wherein $R_{13}$ is hydrogen, lower alkyl, cycloalkyl, or cycloalkylalkyl and $R_{14}$ is hydrogen, lower alkyl, cycloalkyl, cycloalkylalkyl, aminocarbonylalkyl, cyanoalkyl, carboxyalkyl, or alkoxycarbonylalkyl; and E is (1) absent;

(2) —$OR_{15}$ wherein $R_{15}$ is hydrogen, lower alkyl, cycloalkyl, or cycloalkylalkyl; or (3) —$NR_{16}R_{17}$ wherein $R_{16}$ and $R_{17}$ are independently selected from hydrogen, lower alkyl, cycloalkyl, cycloalkylalkyl, and —$(CH_2)_p$—Y wherein p is two to eight and Y is —OH, heterocyclic, —$SO_3H$, —$CO_2R_{18}$ wherein $R_{18}$ is hydrogen or lower alkyl or Y is —$NR_{19}R_{20}$ wherein $R_{19}$ and $R_{20}$ are independently selected from hydrogen, lower alkyl, cycloalkyl, and cycloalkylalkyl; or a pharmaceutically acceptable salt, ester, or prodrug thereof; and compounds of the Formula II $$A-B-C-NH\underset{OP_4}{\overset{R}{\diagdown}}\overset{O}{\underset{\|}{P}}X\diagdown D-E \quad (II)$$

wherein A is hydrogen, an N-protecting group, $R_1NHCH(R_2)C(O)$— wherein $R_1$ is H or an N-protecting group and $R_2$ is hydrogen, lower alkyl, cycloalkyl, cycloalkylalkyl, carboxyalkyl, or alkoxycarbonylalkyl; or A is $HO_2C(CH_2)_nC(O)$— wherein n is one to 3;

B is —$N(R_4)CH(R_3)C(O)$— wherein $R_4$ is hydrogen or lower alkyl and $R_3$ is lower alkyl, cycloalkyl, or cycloalkylalkyl;

C is —$N(R_5)CH(R_6)C(O)$— wherein $R_5$ is hydrogen or lower alkyl and $R_6$ is hydrogen, lower alkyl, cycloalkyl, or cycloalkylalkyl;

R is lower alkyl, cycloalkyl, cycloalkylalkyl, aryl, or bicyclic heterocyclic;

$P_4$ is hydrogen, lower alkyl, or benzyl;

X is —$CH_2$— or —$C(O)$—;

D is (1) —$OR_7$ wherein $R_7$ is hydrogen, lower alkyl, cycloalkyl, or cycloalkylalkyl;

(2) —$NR_8R_9$ wherein $R_8$ and $R_9$ are independently selected from hydrogen, lower alkyl, cycloalkyl, cycloalkylalkyl, and —$(CH_2)_m$—Z wherein m is two to eight and Z is —OH, heterocyclic, —$SO_3H$, —$CO_2R_{10}$ wherein $R_{10}$ is hydrogen or lower alkyl or Z is —$NR_{11}R_{12}$ wherein $R_{11}$ and $R_{12}$ are independently selected from hydrogen, lower alkyl, cycloalkyl, and cycloalkylalkyl;

(3) —$NHCH(R_{13})C(O)$— wherein $R_{13}$ is hydrogen, lower alkyl, cycloalkyl, or cycloalkylalkyl; or (4) —$NHCH(R_{13})C(O)NHCH(R_{14})C(O)$— wherein $R_{13}$ is hydrogen, lower alkyl, cycloalkyl, or cycloalkylalkyl and $R_{14}$ is hydrogen, lower alkyl, cycloalkyl, cycloalkylalkyl, aminocarbonylalkyl, cyanoalkyl, carboxyalkyl, or alkoxycarbonylalkyl; and E is (1) absent;

(2) —$OR_{15}$ wherein $R_{15}$ is hydrogen, lower alkyl, cycloalkyl, or cycloalkylalkyl; or (3) —$NR_{16}R_{17}$ wherein $R_{16}$ and $R_{17}$ are independently selected from hydrogen, lower alkyl, cycloalkyl, cycloalkylalkyl, and —$(CH_2)_p$—Y wherein p is two to eight and Y is —OH, heterocyclic, —$SO_3H$, —$CO_2R_{18}$ wherein $R_{18}$ is hydrogen or lower alkyl or Y is —$NR_{19}R_{20}$ wherein $R_{19}$ and $R_{20}$ are independently selected from hydrogen, lower alkyl, cycloalkyl, and cycloalkylalkyl; or a pharmaceutically acceptable salt, ester, or prodrug thereof; and compounds of the Formula III

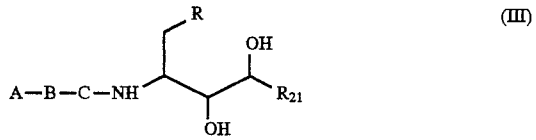

wherein A is hydrogen, an N-protecting group, $R_1NHCH(R_2)C(O)$— wherein $R_1$ is H or an N-protecting group and $R_2$ is hydrogen, lower alkyl, cycloalkyl, cycloalkylalkyl, carboxyalkyl, or alkoxycarbonylalkyl, or arylalkoxycarbonylalkyl; or A is $HO_2C(CH_2)_nC(O)$— wherein n is one to 3; or A is $R_{1a}C(O)$— or $R_{1a}S(O)_2$— wherein $R_{1a}$ is heterocyclic; or A is (aminoalkyl) (alkyl)aminocarbonyl, (alkylaminoalkyl)(alkyl)aminocarbonyl, (dialkylaminoalkyl)(alkyl)aminocarbonyl, (aminoalkyl) (alkyl)aminosulfonyl, (alkylaminoalkyl(alkyl) aminosulfonyl, (dialkylaminoalkyl)(alkyl)aminosulfonyl, (heterocyclicalkyl)(alkyl)aminocarbonyl, or (heterocyclicalkyl)(alkyl)aminosulfonyl;

B is —$N(R_4)CH(R_3)C(O)$— wherein $R_4$ is hydrogen or lower alkyl and $R_3$ is lower alkyl, cycloalkyl, or cycloalkylalkyl;

C is —$N(R_5)CH(R_6)C(O)$— wherein $R_5$ is hydrogen or lower alkyl and $R_6$ is lower alkyl, cycloalkyl, or cycloalkylalkyl;

R is lower alkyl, cycloalkyl, cycloalkylalkyl, aryl, or bicyclic heterocyclic; and $R_{21}$ is lower alkyl, cycloalkyl, or cycloalkylalkyl; or a pharmaceutically acceptable salt, ester, or prodrug thereof.

European Published Patent Application EP 0518299A2, published Dec. 16, 1992, discloses compounds of Formula I

wherein $R_1$, $R_2$, and $R_3$ each represent hydrocarbon groups which may be substituted, except cases in which (1) $R_2$ is unsubstituted methyl, (2) $R_3$ is an unsubstituted hydrocarbon group having one to three carbon atoms, and (3) $R_1$ is benzyloxycarbonylamino-methyl, $R_2$ is isobutyl, and $R_3$ is isobutyl or phenylmethyl. The compounds were disclosed as having endothelin converting enzyme inhibiting activity.

Bertenshaw S R, et al, *Journal of Medicinal Chemistry* 1993;36:173 discloses compounds of the formula

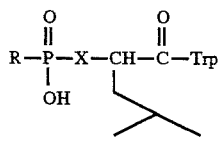

wherein X is $CH_2$, NH, or O;

Japanese Published Patent Application 04327592A, published Nov. 17, 1992, discloses compounds of Formula I

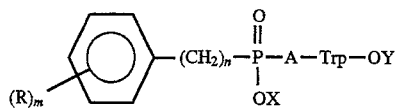

A=leucine, isoleucine, or phenylalanine residue;
Trp=tryptophan residue;
R=lower alkyl, lower alkoxy, or halogen;
X=H or alkali metal;
Y=H, alkali metal, or lower alkyl;
m=0–3;
n=1–4.

R is n-propyl, OEt, Bn, or cyclohexylmethyl as inhibitors of endothelin converting enzyme. The enzyme used in the study was a phosphoramidon sensitive metalloprotease obtained from rabbit lung homogenate.

However, the compounds disclosed in JP 04041430-A, WO 92/12170, WO 92/01468, WO 92/13545, EP 0518299A2, and *Journal of Medicinal Chemistry* 1993;36:173 do not disclose or suggest the novel hydroxamate peptides of the present invention described hereinafter.

SUMMARY OF THE INVENTION

Accordingly, the present invention is a compound of Formula I

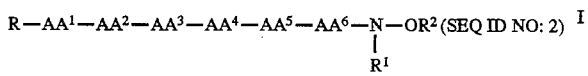

wherein R is hydrogen,

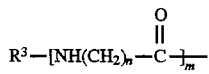

wherein $R^3$ is hydrogen or

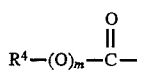

wherein $R^4$ is alkyl, aryl, or arylalkyl, and
m is zero or an integer of one and
n is an integer of one to ten or

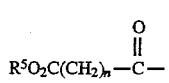

wherein $R^5$ is hydrogen or alkyl, and
n is as defined above;

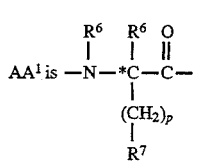

wherein $R^6$ is hydrogen or methyl,
$R^7$ is aryl or heteroaryl, and
p is zero or an integer of one to four or AA$^1$ is absent;

AA$^2$ is 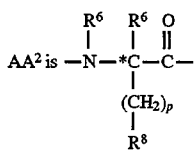

wherein R$^8$ is hydrogen, alkyl, alkenyl, or cycloalkyl, and R$^6$ and p are as defined above or AA$^2$ is absent;

AA$^3$ is 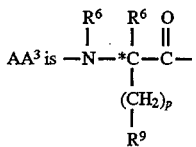

wherein R$^9$ is hydrogen,

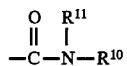

wherein R$^{10}$ and R$^{11}$ are each independently the same or different and each is hydrogen, alkyl, cycloalkyl or —(CH$_2$)$_q$-aryl, wherein q is zero or an integer of one or two or

wherein R$^{10}$ is as defined above and
R$^6$ and p are as defined above or
AA$^3$ is absent;
AA$^4$ and AA$^5$ are each independently

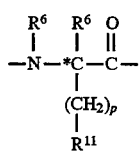

wherein R$^{11}$ is hydrogen, alkyl, alkenyl, or cycloalkyl, and R$^6$ and p are as defined above or one of AA$^4$ or AA$^5$ is absent;

AA$^6$ is 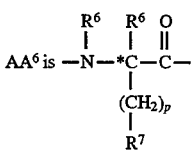

wherein R$^6$, R$^7$, and p are as defined above;
R$^1$ is hydrogen or alkyl;
R$^2$ is hydrogen, arylalkyl or alkyl;
the stereochemistry at *C in AA$^1$, AA$^2$, AA$^3$, AA$^4$, AA$^5$, or AA$^6$ is L, D, or DL; or a pharmaceutically acceptable salt thereof.

Elevated levels of endothelin have been postulated to be involved in a number of pathophysiological states including diseases associated with the cardiovascular system as well as various metabolic and endocrinological disorders. As inhibitors of endothelin converting enzyme, the compounds of Formula I are useful in the treatment of hypertension, myocardial infarction, metabolic, endocrinological and neurological disorders, congestire heart failure, endotoxic and hemorrhagic shock, septic shock, subarachnoid hemorrhage, arrhythmias, asthma, acute and chronic renal failure, cyclosporin-A induced nephrotoxicity, restenosis, angina, ischemic disease, gastric mucosal damage, ischemic bowel disease, cancer, pulmonary hypertension, preeclampsia, atherosclerotic diseases including Raynaud's disease, cerebral vasospasm, and diabetes.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from two to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "cycloalkyl" means a saturated hydrocarbon ring which contains from three to 12 carbon atoms, for example, cyclopropyl, cyclobutyl, cyclopentyl, cyclohexyl, adamantyl, and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, 3,3-diphenylalanyl, 10,11-dihydro-5H-dibenzo-[a,d]-(cyclohepten-5-yl)glycyl, or a fluorenyl group and the like, unsubstituted or substituted by one to four substituents selected from alkyl as defined above, alkoxy as defined above, thioalkoxy as defined above, hydroxy thiol nitro, halogen, amino;

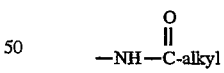

wherein alkyl is as defined above,

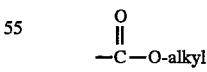

wherein alkyl is as defined above,

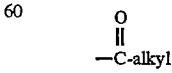

wherein alkyl is as defined above, or aryl.

The term "arylalkyl" means an aromatic radical attached to an alkyl radical wherein aryl and alkyl are as defined above, for example, benzyl, fluorenylmethyl, and the like.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7- indolyl, N-formyl- 2-, 3-, 4-, 5-, 6-, 7- indolyl, 2 -, 3 -, 4-, 5 -, 6 -, 7-benzo[b] thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by one to two substituents selected from alkyl as defined above, aryl as defined above, alkoxy as defined above, thioalkoxy as defined above, hydroxy, thiol, nitro, halogen, formyl, amino;

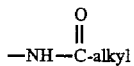

wherein alkyl is as defined above,

wherein alkyl is as defined above

wherein alkyl is as defined above, or phenyl.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

"Noble metal" is platinum, palladium, rhodium, ruthenium, and the like.

"Halogen" is fluorine, chlorine, bromine, or iodine.

The following table provides a list of abbreviations and definitions thereof used in the present invention.

| Abbreviation* | Amino Acid |
|---|---|
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

| Abbreviation* | Modified and Unusual Amino Acid |
|---|---|
| Nva | Norvaline |

-continued

| | |
|---|---|
| Nle | Norleucine |
| Alg | 2-Amino-4-pentanoic acid (allylglycine) |
| Cpn | 2-Amino-3-cyclopropane propanoic acid (Cyclopropylalanine) |
| Chx | Cyclohexylalanine (Hexahydrophenylalanine) |
| His (Dnp) | $N^{im}$-2,4-Dinitrophenyl - histidine |
| HomoPhe | 2-Amino-5-phenylpentanoic acid (homophenylalanine) |
| 1-Nal | 3-(1'-Naphthyl)alanine |
| 2-Nal | 3-(2'-Naphthyl)alanine |
| Pgy | 2-Aminopentanoic acid (Propylglycine) |
| Pyr | 2-Amino-3-(3-pyridyl)-propanoic acid (3-Pyridylalanine) |
| Tza | 2-Amino-3-(4-thiazolyl)-propanoic acid |
| Tyr (Ot-Bu) | O-tertiary butyltyrosine |
| Tyr (OMe) | O-methyltyrosine |
| Tyr (OEt) | O-ethyltyrosine |
| Trp (For) | $N^{in}$-Formyltryptophan |
| His (t-Bu) | $N^{im}$-tertiary butylhistidine |
| His (C$\phi_3$) | $N^{im}$-triphenylmethyl-histidine ($N^{im}$-tritylhistidine) |
| Trp (Me) | $N^{in}$-Methyltryptophan |
| Asp (Ot-Bu) | Aspartic acid 4-tertiary butyl ester |
| Asp (OMe) | Aspartic acid 4-methyl ester |
| Asp (OBn) | Aspartic acid 4-benzyl ester |
| Glu (Ot-Bu) | Glutamic acid 5-tertiary butyl ester |
| Glu (OMe) | Glutamic acid 5-methyl ester |
| Bta | 3-Benzothienyl alanine |
| Bfa | 3-Benzofuranyl alanine |

| Abbreviation | Protecting Group |
|---|---|
| Ac | Acetyl |
| Acm | Acetamidomethyl |
| Ada | 1-Adamantyl acetic acid |
| Adoc | Adamantyloxycarbonyl |
| CBZ | Benzyloxycarbonyl |
| 2-Br-CBZ | ortho-Bromobenzyloxy-carbonyl |
| 2-Cl-CBZ | ortho-Chlorobenzyloxy-carbonyl |
| Bom | Benzyloxymethyl |
| Boc | tertiary Butyloxycarbonyl |
| TBS | tertiary Butyldimethyl-silyl |
| Dnp | 2,4-Dinitrophenyl |
| For | Formyl |
| Fmoc | 9-Fluorenylmethyloxy-carbonyl |
| NO$_2$ | Nitro |
| Tos | 4-Toluenesulfonyl (tosyl) |
| Trt | Triphenylmethyl (trityl) |
| Bn | Benzyl |
| O-Bn | O-Benzyl |
| O-Me | O-Methyl |
| Ph | Phenyl |

| Abbreviation | Solvents and Reagents |
|---|---|
| HOAc | Acetic acid |
| CH$_3$CN | Acetonitrile |
| CH$_2$Cl$_2$ or DCM | Dichloromethane |
| DCC | N,N'-Dicyclohexyl-carbodiimide |
| DMAP | 4-dimethylaminopyridine |
| DIEA | N,N-Diisopropylethylamine |
| DMF | Dimethylformamide |
| HCl | Hydrochloric acid |

| | -continued |
|---|---|
| HF | Hydrofluoric acid |
| HOBt | 1-Hydroxybenzotriazole |
| KOH | Potassium hydroxide |
| TFA | Trifluoroacetic acid |
| EDAC | Ethyl-3-(3-dimethylamino-propyl)carbodiimide hydrochloride |
| NaHCO$_3$ | Sodium bicarbonate |
| NaCl | Sodium chloride |
| NaCNBH$_4$ | Sodium cyanoborohydride |
| MgSO$_4$ | Magnesium sulfate |
| LAH | Lithium aluminum hydride |
| KHSO$_4$ | Potassium bisulfate |
| MeOH | Methanol |
| CHCl$_3$ | Chloroform |
| TEA or Et$_3$N | Triethylamine |
| THF | Tetrahydrofuran |
| EtOAc | Ethyl acetate |
| N$_2$ | Nitrogen |
| NaN$_3$ | Sodium azide |
| DMSO | Dimethylsulfoxide |
| EDTA | Ethylenediamine tetraacetic acid |
| MBHA Resin | Methylbenzhydrylamine resin |
| Sasrin Resin | 2-methoxy-4-alkoxybenzyl alcohol resin |

*If the optical activity of the amino acid is other than L (S), the amino acid or abbreviation is preceded by the appropriate configuration D (R) or DL (RS).

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S M, et al, "Pharmaceutical Salts," *J of Pharma Sci* 1977;66:1.

The acid addition salts of said basic compounds are prepared by contacting the free base form with a sufficient amount of the desired acid to produce the salt in the conventional manner. Preferably, a peptide of Formula I can be converted to an acidic salt by treating with an aqueous solution of the desired acid, such that the resulting pH is less than four. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free base form may be regenerated by contacting the salt form with a base and isolating the free base in the conventional manner.

The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloro-procaine, choline, diethanolamine, dicyclohexylamine, ethylenediamine, N-methylglucamine, and procaine (see, for example, Berge S M, et al, "Pharmaceutical Salts," *J of Pharma Sci,* 1977;66:1.

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than 9. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free acid form my be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein

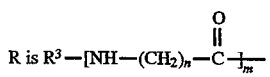

wherein R$^3$ is hydrogen,
tert-butyloxycarbonyl,
carbobenzyloxy, 9-fluorenylmethyloxycarbonyl,
benzyl,
acetyl, or
phthaloyl,
n is an integer of one to ten,
m is zero or an integer of one or

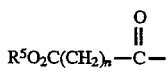

wherein R$^5$ is hydrogen, or alkyl and
n is as defined above;
AA$^1$ is His,
His (t-Bu),
His (C(Ph)$_3$), Tza,
Phe,
Tyr,
Tyr(OMe),
Tyr(Ot-Bu)
1-Nal,
2-Nal,
Pyr,
HomoPhe,
Trp,
Trp(For), or
Trp(Me), or
$AA^1$ is absent;
$AA^2$ is Leu,
Ile,
Nle,
Val,
Nva,
Ala,
Chx,
Gly,
Alg,
Cpn, or
Pgy, or
$AA^2$ is absent;
$AA^3$ is Asp,
Ash,
Glu,
Gln,
Asp(Ot-Bu),
Asp(OMe),
Glu(Ot-Bu), or
Glu (OMe), or
$AA^3$ is absent;
$AA^4$ and $AA^5$ are both independently
Leu,
Ile,
Nle,
Val,
Nva,
Ala,
Chx,
Gly,
Alg,
Cpn, or
Pgy, or
one of $AA^4$ or $AA^5$ is absent;
$AA^6$ is Trp,
Trp(For),
Trp(Me),
His,
Phe,
Tyr(OMe),
Tyr(Ot-Bu),
1-Nal,
2-Nal,
Bta,
Bfa,
Pyr, or
HomoPhe;
$R^1$ and $R^2$ are hydrogen.

Particularly valuable are:
Ile-Ile-Trp-NHOH;
Boc-Ile-Ile-Trp-NHOH;

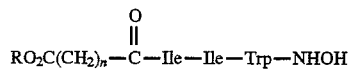

wherein R is hydrogen,
methyl,
ethyl, or
t-butyl, and
n is an integer of one to ten;

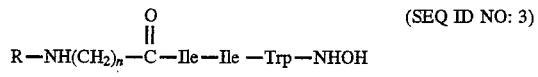 (SEQ ID NO: 3)

wherein R is hydrogen,
Boc, or
CBZ, and
n is an integer of one to ten;
Asp-Ile-Ile-Trp-NHOH (SEQ ID NO: 4);
Boc-Asp-Ile-Ile-Trp-NHOH (SEQ ID NO: 4);

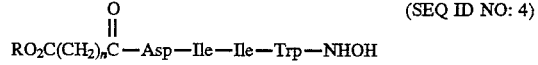 (SEQ ID NO: 4)

wherein R is hydrogen,
methyl,
ethyl, or
t-butyl, and
n is an integer of one to ten;

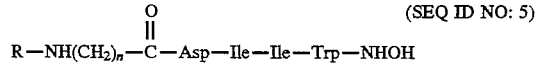 (SEQ ID NO: 5)

wherein R is hydrogen,
Boc, or
CBZ, and
n is an integer of one to ten;
Leu-Asp-Ile-Ile-Trp-NHOH (SEQ ID NO: 6);
Boc-Leu-Asp-Ile-Ile-Trp-NHOH (SEQ ID NO: 6);

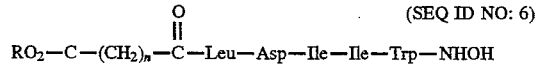 (SEQ ID NO: 6)

wherein R is hydrogen,
methyl,
ethyl, or
t-butyl, and
n is an integer of one to ten;

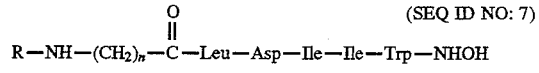 (SEQ ID NO: 7)

wherein R is hydrogen,
Boc, or
CBZ, and
n is an integer of one to ten;
His-Leu-Asp-Ile-Ile-Trp-NHOH (SEQ ID NO: 8);
Boc-His-Leu-Asp-Ile-Ile-Trp-NHOH (SEQ ID NO: 8);

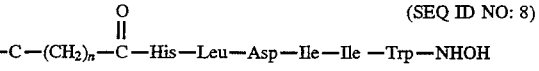 (SEQ ID NO: 8)

wherein R is hydrogen,
methyl,
ethyl, or t-butyl, and
n is an integer of one to ten;

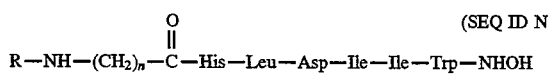
(SEQ ID NO: 9)

wherein R is hydrogen,
Boc, or
CBZ, and
n is an integer of one to ten;
Ile-Ile-Phe-NHOH;
Boc-Ile-Ile-Phe-NHOH;

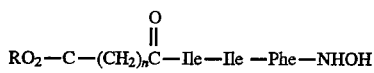

wherein R is hydrogen,
methyl,
ethyl, or
t-butyl, and
n is an integer of one to ten;

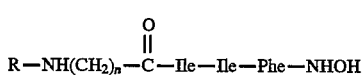
(SEQ ID NO: 10)

wherein R is hydrogen,
Boc, or
CBZ, and
n is an integer of one to ten;
Ile-Ile-1-Nal-NHOH;
Boc-Ile-Ile-1-Nal-NHOH;

wherein R is hydrogen,
methyl,
ethyl, or
t-butyl, and
n is an integer of one to ten;

(SEQ ID NO: 11)

wherein R is hydrogen,
Boc, or
CBZ, and
n is an integer of one to ten;
Ile-Ile-2-Nal-NHOH;
Boc-Ile-Ile-2-Nal-NHOH;

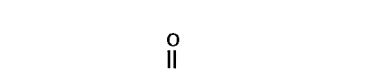

wherein R is hydrogen,
methyl,
ethyl, or
t-butyl, and
n is an integer of one to ten;

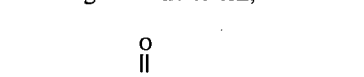
(SEQ ID NO: 11)

wherein R is hydrogen,
Boc, or
CBZ, and n is an integer of one to ten;
Ile-Ile-Bta-NHOH;
Boc-Ile-Ile-Bta-NHOH;

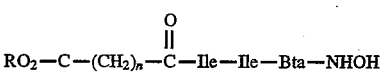

wherein R is hydrogen,
methyl,
ethyl, or
t-butyl, and
n is an integer of one to ten;

(SEQ ID NO: 11)

wherein R is hydrogen,
Boc, or
CBZ, and
n is an integer of one to ten;
Ile-Ile-Bfa-NHOH;
Boc-Ile-Ile-Bfa-NHOH;

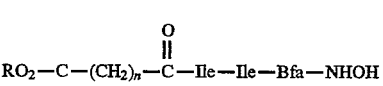

wherein R is hydrogen,
methyl,
ethyl, or
t-butyl, and
n is an integer of one to ten;

(SEQ ID NO: 11)

wherein R is hydrogen,
Boc, or
CBZ, and
n is an integer of one to ten;
Asp-Ile-Ile-Phe-NHOH (SEQ ID NO: 12);
Boc-Asp-Ile-Ile-Phe-NHOH (SEQ ID NO: 12);

(SEQ ID NO: 12)

wherein R is hydrogen,
methyl,
ethyl, or
t-butyl, and
n is an integer of one to ten;

(SEQ ID NO: 13)

wherein R is hydrogen,
Boc, or
CBZ, and
n is an integer of one to ten;
Asp-Ile-Ile-1-Nal-NHOH (SEQ ID NO: 14);
Boc-Asp-Ile-Ile-1-Nal-NHOH (SEQ ID NO: 14);

(SEQ ID NO: 14)

wherein R is hydrogen,
Boc, or
CBZ, and
n is an integer of one to ten;

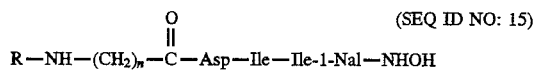

R—NH—(CH₂)ₙ—C(=O)—Asp—Ile—Ile-1-Nal—NHOH  (SEQ ID NO: 15)

wherein R is hydrogen,
BOC, or
CBZ, and
n is an integer of one to ten;
Asp-Ile-Ile-2-Nal-NHOH (SEQ ID NO: 14);
Boc-Asp-Ile-Ile-2-Nal-NHOH (SEQ ID NO: 14);

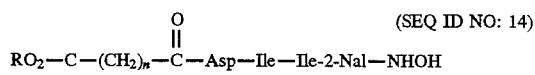

RO₂—C—(CH₂)ₙ—C(=O)—Asp—Ile—Ile-2-Nal—NHOH  (SEQ ID NO: 14)

wherein R is hydrogen,
Boc, or
CBZ, and
n is an integer of one to ten;

R—NH—(CH₂)ₙ—C(=O)—Asp—Ile—Ile-2-Nal—NHOH  (SEQ ID NO: 15)

wherein R is hydrogen,
Boc, or
CBZ, and
n is an integer of one to ten; or a pharmaceutically acceptable salt thereof.

The compounds of Formula I are valuable inhibitors of endothelin converting enzyme. The test employed indicates that the compounds of Formula I possess inhibitory activity towards an endothelin converting enzyme.

SCREENING OF ENDOTHELIN CONVERTING ENZYME (ECE) INHIBITORS

ECE Activity Assay: The typical reaction mixture (50 μL) contained 10 μM big ET, 100 mM Hepes-KOH (pH 7.0), 0.25% Triton X-100, 0.01% NaN₃, 0.2 mM phenylmethylsulfonyl fluoride, 50 μM pepstatin A, 0.1 mM leupeptin, the indicated concentration of compound (or DMSO for control), and the indicated amount of protein. The final DMSO concentration was kept at 3%. After incubation for 1.5 hours at 37° C., the reaction was stopped by the addition of EDTA to a final concentration of 10 mM. This final mixture was diluted (usually 100-fold) with the radioimmunoassay buffer (see below) and used for radioimmunoassay.

Radioimmunoassay (RIA): For the measurement of immunoreactive (ir) ET-1, the assay mixture (250 μL) contained the antibody against ET-1, an ET-1 sample, and [¹²⁵I]ET-1 (7000 cpm) in the radioimmunoassay buffer (60 mM potassium phosphate (KPi), pH 7.4/10 mM, EDTA/8 mM, NaN₃/3% DMSO/0.1% bovine serum albumin/0.1% Tween 20). The order of the addition was ET-1 sample, followed by antibody, then [¹²⁵I]ET-1. After incubation at 4° C. for 0.5 to 2 days, unbound ET-1 was co-precipitated by the addition of charcoal (2.4%, w/v)/dextran (0.24%, w/v) suspension (125 μL) in the RIA buffer with BSA replacedby gelatin (0.25%, w/v). The amount of ir-ET-1 was measured by counting the supernatant and determined from the standard curve. The cross-reactivity to big ET-1 was less than 0.01% and the detection limit was 1 Fmol.

TABLE II
Biological Activity of Compounds of Formula I

| Example Number | Compound | Conc. (μM) | % ECE Inhibition |
|---|---|---|---|
| 2 | Boc—Ile—Ile—Trp—NHOH | 100 | 47 |
| 3 | Boc—Ile—Ile—D—Trp—NHOH | 100 | 46 |
| 4 | Boc—Ile—Trp—NHOH | 100 | 44 |
| 6 | Ile—Ile—Trp—NHOH | 100 | 74 |
| 8 | H₃CO₂C(CH₂)₂—C(=O)—Ile—Ile—Trp—NHOH | 4 / 20 | 34 / 68 |
| 10 | HO₂C(CH₂)₂—C(=O)—Ile—Ile—Trp—NHOH | IC₅₀ = 4.7 μM | |
| 12 | H₂N(CH₂)₁₀—C(=O)—Ile—Ile—Trp—NHOBn (SEQ ID NO: 3) | 100 | 65 |
| 13 | H₂N(CH₂)₁₀—C(=O)—Ile—Ile—Trp—NHOH (SEQ ID NO: 3) | 10 / 50 | 22 / 57 |
| 22 | Boc—Asp—Ile—Ile—Trp(For)-NHOH (SEQ ID NO: 4) | 10 / 40 / 100 | 53 / 73 / 87 |

An alternative method to prepare compounds of the present invention is described using conventional solid phase peptide chemistry techniques. The linear peptides are prepared by standard solid phase synthetic peptide methodology utilizing a Fmoc/benzyl strategy (Stewart J M, Young J D, Solid Phase Peptide Synthesis, Pierce Chemical Co., Rockford, Ill., 1984). All protected amino acids and reagents are obtained from commercial sources and are not further purified. The protected peptide resin, such as Sasrin resin, is prepared on an Applied Biosystems 430A Peptide Synthesizer utilizing protocols supplied for a dicyclohexylcarbodiimide-mediated coupling scheme (Standard 1.0, Version 1.4). Amino acid side-chains are protected as follows: Bn(Asp, Glu, Ser, Thr), 2-Cl-Z(Lys), DNP(His), and ACM(Cys). Fmoc deprotection at each step is effected by treatment with piperidine in a suitable solvent such as CH₂Cl₂. A typical cycle for the coupling of an individual amino acid is illustrated below (reproduced from the ABI manual):

Schedule for Solid Phase Peptide Synthesis (use of Fmoc amino acids)

| Step | Reagent | Vol (mL) | Time (min) |
|---|---|---|---|
| 1 | DCM wash (2 times) | 15 | 3 |
| 2 | DMF wash (2 times) | 15 | 3 |
| 3 | Deprotect: DMF:piperidine (1:1) | 15 | 20 |
| 4 | DMF wash (2 times) | 15 | 3 |
| 5 | Dioxane:water (2:1) (2 times) | 15 | 10 |
| 6 | DMF wash (3 times) | 15 | 5 |
| 7 | DCM wash (3 times) (or DMF) | 15 | 5 |
| 8 | Symmetrical anhydride of Fmoc amino acid in DCM (or DMF:DCM) (use 2 or 3 moles of anhydride) | 15 | 15 |

-continued

Schedule for Solid Phase Peptide Synthesis
(use of Fmoc amino acids)

| Step | Reagent | Vol (mL) | Time (min) |
|---|---|---|---|
| 9 | Add 1.0 mL of 10% DIEA in DCM | 1 | 15 or until monitoring shows coupling complete |
| 10 | Recouple if necessary by repeating Steps 7–9 | | 40 |
| 11 | DMF wash (5 times) | 15 | 8 |
| 12 | iPrOH wash (5 times) | 15 | 8 |
| 13 | DCM wash (5 times) | 15 | 8 |

The peptide is liberated from the solid support using 2% TFA/CH$_2$Cl$_2$. The peptide is treated with benzyloxyamine in the presence of activating agents as described hereinafter under solution peptide synthesis of compounds of Formula I. The benzylhydroxamic derivative and the side-chains are then deprotected under hydrogenation conditions using Pd/BaSO$_4$ as the catalyst. The crude peptide is purified by reverse phase HPLC.

AA$^6$—NH—OBn    V wherein AA$^6$ is as defined above in the presence of a coupling reagent such as, for example, EDAC/HOBt and the like, and a solvent such as, for example, DMF and the like, to afford a compound of Formula II R—AA$^1$—AA$^2$—AA$^3$—AA$^4$—AA$^5$—AA$^6$—NH—OBn (SEQ ID NO: 2)    II wherein R, AA$^1$, AA$^2$, AA$^3$, AA$^4$, AA$^5$, and AA$^6$ are as defined above.

A compound of Formula II is hydrogenated in the presence of a catalyst such as, for example, palladium on barium sulfate and the like, and a solvent such as, for example, methanol and the like, to afford after removal of protecting groups by conventional methodology a compound of Formula I.

The compounds of Formula I also may be prepared by conventional solution peptide synthesis. Preferred methods for the preparation of compounds of Formula I are described in Schemes I to VI.

SCHEME I

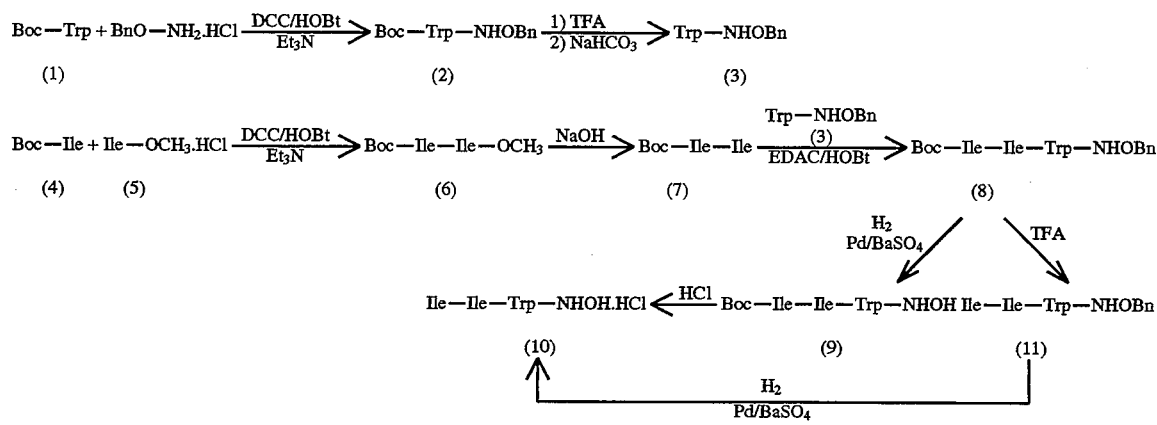

Thus, the hydroxamate peptides can be prepared on the resin. The hydroxamate peptides are prepared by sequential stepwise coupling of the amino acids selected from R-AA$^1$, AA$^2$, AA$^3$, AA$^4$, and AA$^5$ to the preceding amino acid using solid-phase peptide chemistry as described above. The peptide is liberated from the solid support by transesterification with an alcohol such as, for example, methanol, and the like, in the presence of a base such as, for example, triethylamine and the like, to afford a peptide ester of Formula IV

R—AA$^1$—AA$^2$—AA$^3$—AA$^4$—AA$^5$—OR$^{12}$ (SEQ ID NO: 16)    IV wherein R$^{12}$ is alkyl and R, AA$^1$, AA$^2$, AA$^3$, AA$^4$, and AA$^5$ are as defined above. The ester of Formula IV is hydrolyzed with a base such as, for example, an alkali metal hydroxide, for example, sodium hydroxide, potassium hydroxide, and the like, to afford an acid of Formula III

R—AA$^1$—AA$^2$—AA$^3$—AA$^4$—AA$^5$—OH (SEQ ID NO: 16)    III wherein R, AA$^1$, AA$^2$, AA$^3$, AA$^4$, and AA$^5$ are as defined above. The acid of Formula III is coupled to a compound of Formula V

SCHEME II

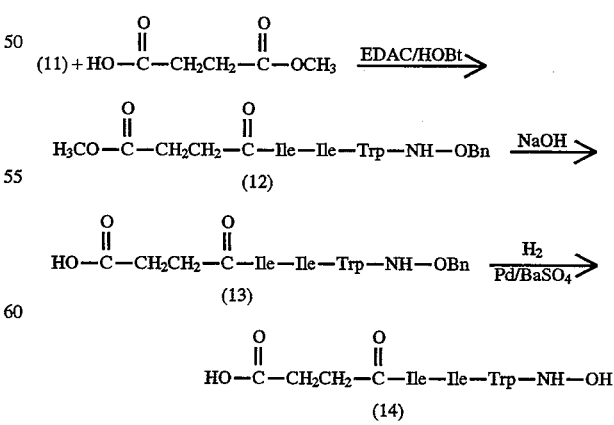

SCHEME III

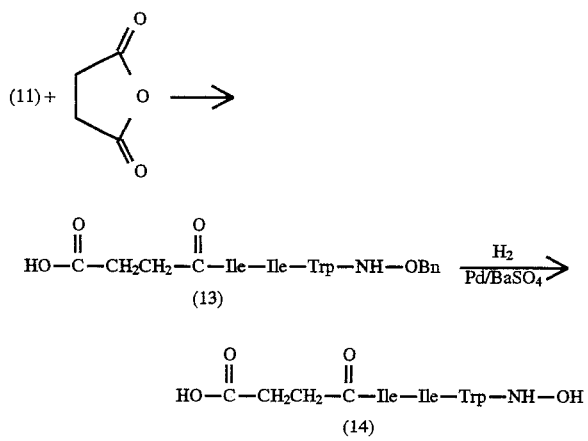

SCHEME IV

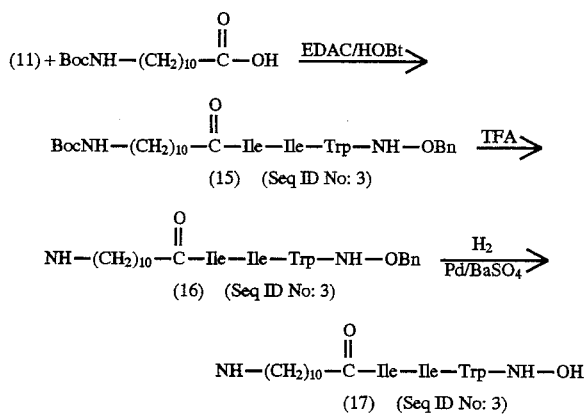

SCHEME V

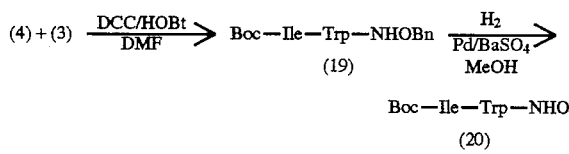

SCHEME VI

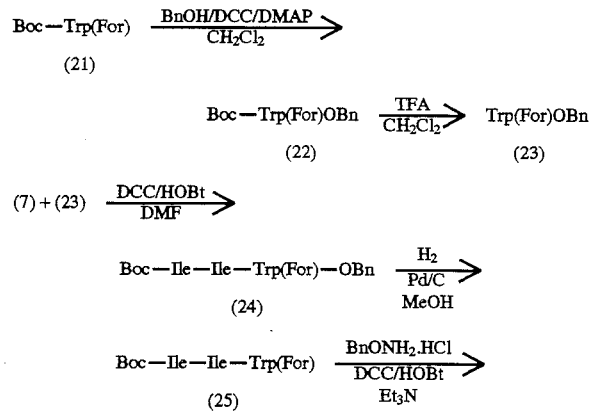

SCHEME VI -continued

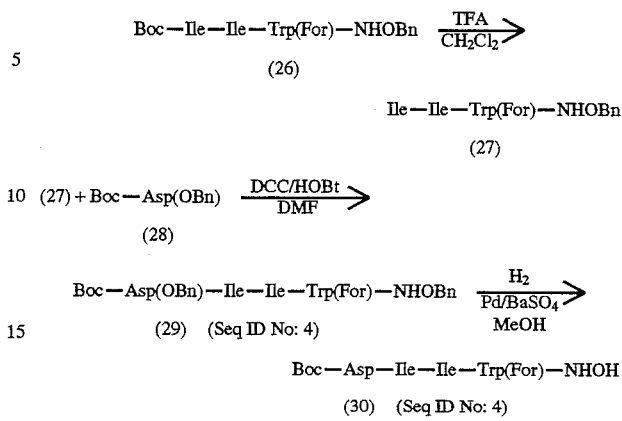

Compounds of Formula I are designated by numbers 8, 9, 10, 11, 12, 13, 14, 15, 16, 17, 19, 20, 26, 27, 29, and 30.

These schemes illustrate preferred methods from which a person, skilled in the art, could analogously prepare all compounds of Formula I.

Compounds designated 8 through 11 are prepared as outlined in Scheme I. Thus, Compound 1 is reacted with O-benzylhydroxylamine hydrochloride in the presence of a coupling reagent such as, for example, DCC/HOBt/Et$_3$N; EDAC.HCl/Et$_3$N, and the like, and a solvent such as, for example, DMF and the like. Alternatively, a conventional mixed anhydride procedure may be used employing methyl, ethyl, or isobutyl chloroformate and a base such as, for example, N-methylpiperidine, morpholine, and the like. The coupling reaction is carried out at about 0° C. to about room temperature for about 3 to about 24 hours to afford the Compound 2. Preferably, the reaction is carried out with DCC/HOBt/Et$_3$N in DMF at 0° C. for about 12 to about 15 hours. Compound 2 is treated with an acid such as, for example, TFA, HCl, and the like, in a solvent such as, for example, CH$_2$Cl$_2$ and the like, at about room temperature for about 1 to about 3 hours to afford Compound 3. Preferably, the reaction is carried out with TFA and CH$_2$Cl$_2$ at about room temperature for about 1 hour.

Compound 6 is prepared by reacting Compound 4 with Compound 5 in the presence of an activating agent such as described above, for example, DCC/HOBt, EDAC.HCl/HOBt, and a base, for example, Et$_3$N or a mixed anhydride procedure as described above, for example, methyl, ethyl, or isobutyl chloroformate and a base, for example, N-methylpiperidine, morpholine, and the like, in an inert solvent such as, for example, CH$_2$Cl$_2$, CHCl$_3$, DMF, and the like, at about 0° C. to about room temperature for about 14 hours to afford Compound 6. Preferably, the reaction is carried out with DCC/HOBt and Et$_3$N in DMF. The methyl ester of Compound 6 is hydrolyzed with a base such as, for example, an aqueous solution of NaOH, LiOH, KOH, and the like, in a solvent such as, for example, THF, ethanol, methanol, and the like, at about room temperature for about 12 to about 16 hours to afford the acid (Compound 7). Preferably, the reaction is carried out with 1.1 equivalents of aqueous NaOH in THF at about room temperature for about 12 to about 16 hours. Compound 8 is prepared by reacting Compound 3 with Compound 7 using the coupling conditions used to prepare Compound 6 from Compounds 4 and 5 to afford Compound 8. Compound 8 is hydrogenated at 5 to 50 pounds per square inch (psi) hydrogen in the presence of a catalyst such as, for example, palladium on carbon (5–20%) palladium on barium sulfate (5%), and the like, and a solvent such as, for example, methanol, ethanol, THF, dioxane, and the like, to afford Compound 9. Preferably, the reaction is carried out in the presence of 5% palladium on barium sulfate in methanol. Compound 9 is treated with an acid such as, for example, TFA, HCl, and the like, in a solvent such as, for example, $CH_2Cl_2$ and the like, at about room temperature for about 1 to about 3 hours to afford Compound 10. Preferably, the reaction is carried out with TFA at about room temperature for about 1 to about 3 hours. Using the methodology used to convert Compound 9 to Compound 10, one obtains Compound 11 from Compound 8. Compound 11 can be converted to Compound 10 using the methodology used to convert Compound 8 to Compound 9.

Compounds designated 12 to 14 are prepared as outlined in Scheme II. Thus, Compound 11 is reacted with monomethyl succinate in the presence of an activating agent such as, for example, DCC/HOBt, EDAC.HCl/$Et_3N$, and the like, or the mixed anhydride procedure as described above in a solvent such as, for example, DMF and the like at about 0° C. to about room temperature for about 3 hours to about 24 hours to afford Compound 12. Preferably, the reaction is carried out with 1.14 equivalents of mono-methyl succinate and EDAC.HCl/$Et_3N$ in DMF for 14 hours. The methyl ester of Compound 12 is treated with an aqueous base such as, for example, NaOH, LiOH, KOH, and the like, and a solvent such as, for example, THF, ethanol, methanol, dioxane, and the like, at about room temperature for about 7 days to afford the acid (Compound 13). Preferably, the reaction is carried with 2.2 equivalents of aqueous NaOH and THF at about room temperature for about 7 days. The N-benzyloxyamide of Compound 13 is treated with hydrogen at a pressure of 5 to 50 psi in the presence of a catalyst such as, for example, palladium on barium sulfate (5%) and the like, and a solvent such as, for example, methanol and the like, to afford Compound 14. Preferably, the reaction is carried out in the presence of palladium on barium sulfate and methanol. Alternatively, as outlined in Scheme III, Compound 13 is prepared by reacting Compound 11 with succinic anhydride in a solvent such as, for example, THF, dioxane, DMF, acetonitrile, and the like, to afford Compound 13. Preferably, the reaction is carried out in THF. Compound 13 is treated with hydrogen using the methodology described above to prepare Compound 14.

Compounds designated 15–17 are prepared as outlined in Scheme IV. Thus, Compound 15 is prepared by reacting Compound 11 with N-Boc-11-aminoundecanoic acid using the methodology described above for preparing Compound 6. Preferably, the coupling is carried out in the presence of EDAC/HOBt and pyridine. Compound 16 is prepared by treating Compound 15 with an acid such as, for example, TFA, HCl, and the like, in a solvent such as, for example, $CH_2Cl_2$ and the like, at about room temperature for about 1 hour to afford Compound 16. Preferably, the reaction is carried out with TFA in $CH_2Cl_2$ at about room temperature for about 1 hour. Compound 17 is prepared by hydrogenating Compound 16 in the presence of a palladium catalyst such as, for example, palladium on barium sulfate (5%) and the like, and a solvent such as, for example, methanol and the like, as described above to afford Compound 17. Preferably, the reaction is carried out in the presence of palladium on barium sulfate (5%) and methanol.

Compounds designated 19 through 20 are prepared as outlined in Scheme V. Thus, Compound 19 is prepared by reacting Compound 4 with Compound 3 using the methodology described above for preparing Compound 6. Preferably, the coupling is carried out in the presence of DCC/HOBt. Compound 20 is prepared by hydrogenating Compound 19 in the presence of palladium catalyst as described in the preparation of Compound 17 from Compound 16.

Compounds designated 22 through 30 are prepared as outlined in Scheme VI. Thus, Compound 21 is reacted with benzyl alcohol in the presence of coupling agents described earlier. Preferably, the reaction is carried out with DCC/DMAP in $CH_2Cl_2$ at room temperature for about 10 to 17 hours to afford Compound 22. Compound 22 is treated with an acid such as, for example, TFA, HCl, and the like, in a solvent such as, for example, $CH_2Cl_2$, and the like, at about room temperature for about 1 to about 3 hours to afford Compound 23. Compound 23 is reacted with Compound 7 in the presence of coupling agents described earlier. Preferably, the reaction is carried out with DCC/HOBt in DMF at 0° C. to room temperature for about 12 to 16 hours to afford Compound 24.

Compound 24 is hydrogenated at 5 to 50 psi hydrogen in the presence of a palladium catalyst, such as palladium on carbon (20%), and the like, and a solvent such as, for example, methanol, and the like, as described above to afford Compound 25.

Compound 26 is prepared by reacting Compound 25 with O-benzylhydroxylamine hydrochloride in the presence of a coupling agent such as, for example, DCC/HOBt/$Et_3N$, EDAC.HCl/$Et_3N$, and the like, and a solvent such as, for example, DMF, and the like. The coupling reaction is carried out at about 0° C. to about room temperature for about 3 to about 24 hours. Preferably, the reaction is carried out with DCC/HOBt/$Et_3N$ in DMF at 0° C. to room temperature for about 12 to about 15 hours. Compound 26 is treated with an acid such as, for example, TFA, HCl, and the like, in a solvent such as, for example, $CH_2Cl_2$, and the like, at about room temperature for about 1 to about 3 hours to afford Compound 27. Preferably, the reaction is carried out with TFA and $CH_2Cl_2$ at about room temperature for about 1 hour.

Compound 29 is prepared by reactinS Compound 27 with Compound 28 in the presence of an activating agent such as described above, for example, DCC/HOBt, EDAC.HCl/HOBt, and a base, for example, $Et_3N$ or a mixed anhydride procedure as described above in a solvent such as, for example, DMF, and the like, at about 0° C. to about room temperature for about 3 hours to about 24 hours. Preferably, the reaction is carried out with DCC/HOBt in DMF for 14 hours. The N-benzyloxyamide of Compound 29 is treated with hydrogen at a pressure of 5 to 50 psi in the presence of a catalyst such as, for example, palladium on barium sulfate (5%), and the like, and a solvent such as, for example, methanol to afford Compound 30.

All the hydroxamate compounds of Formula I can be prepared by the methods outlined in Schemes I to VI.

The strategy of peptide chain assembly and removal of protecting groups is discussed in Chapter 1, "The Peptide Bond," in "The Peptides. Analysis, Synthesis, Biology," Gross E, Meienhofer J, Eds., Academic Press, New York, N.Y. 1979;1:42.

The DCC/HOBt method of coupling is well known to those skilled in the art and is discussed in Chapter 5, "The Carbodiimide Method" by Rich D H, Singh J, in "The Peptides. Analysis, Synthesis, Biology," Gross E, Meienhofer J, Eds., Academic Press, New York, N.Y. 1979;1:241.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use inhibitors of endothelin converting enzyme the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting example illustrates the inventors' preferred methods for preparing the compounds of the invention.

EXAMPLE 1

Boc-Ile-Ile-Trp-NHOBn(N-[(1,1-dimethylethoxy) carbonyl]-L-isoleucyl-L-isoleucyl-N-(phenylmethoxy)-L-tryptophanamide)

Step 1: Preparation of Boc-Ile-Ile-OCH$_3$(methyl-N-[N-[(1,1-dimethylethoxy)carbonyl]-L-isoleucyl]-L-isoleucine)

A solution of N-Boc-L-isoleucine hemihydrate (26.44 g, 0.11 mol), L-isoleucine methyl ester hydrochloride (20.0 g, 0.11 mol), and HOBt (18.42 g, 0.132 mol) in DMF (300 mL) is treated with triethylamine (37.58 mL, 0.276 mol), followed by DCC (26.08 g, 0.122 mol) at 0° C. The reaction mixture is kept cold for 2 to 3 hours and stirred at room temperature for a total of 21 hours. The suspension is filtered and the filtrate is concentrated. The residue is treated with EtOAc and the solution filtered. The filtrate is washed with saturated aqueous solutions of NaHCO$_3$ and NaCl, dried over Na$_2$SO$_4$, and concentrated. The crude product is suspended in boiling hexane and EtOAc is added portionwise until the solution is homogeneous. The solution is filtered hot, and upon cooling to 0° C., 31.79 g of the title compound is obtained as a white crystalline solid; Mass spectroscopy (chemical ionization) (MS(CI)), M+1=359

Step 2: Preparation of BOc-Ile-Ile([N-[(1,1-dimethyl-ethoxy)carbonyl]-L-isoleucyl]-L-isoleucine)

A solution of Boc-Ile-Ile-OCH₃ (5.0 g, 0.014 mol) in THF (50 mL) is treated dropwise with aqueous 1N NaOH (15 mL, 0.015 mol). After addition is complete the reaction mixture is stirred at room temperature for 16 hours and concentrated. The residue is dissolved in water and the aqueous solution is extracted with diethyl ether. The organic layer is discarded and the pH of the aqueous layer is adjusted to 2 to 3 with aqueous 1N citric acid. The acidic solution is extracted with EtOAc and the organic extract is washed with saturated aqueous NaCl, dried over Na₂SO₄, filtered, and concentrated to give 4.65 g of the title compound as a white foam; MS(CI), M+1=345.

Step 3: Preparation of Boc-Trp-NHOBn(1,1-dimethyl-ethyl (S)-1-(1H-indol-3-ylmethyl)-2-oxo-2-[(phenylmethoxy)amino]carbamate)

A solution of N-α-t-butoxycarbonyl-L-tryptophan (12.0 g, 0.0396 mol), O-benzylhydroxylamine hydrochloride (6.32 g, 0.0396 mol), and HOBt (6.42 g, 0.0475 mol) in DMF (120 mL) is treated with triethylamine (13.8 mL, 0.0992 mol) followed by DCC (9.0 g, 0.0436 mol) at 0° C. The reaction mixture is kept cold for 2 to 3 hours and stirred at room temperature for 22 hours. The suspension is filtered and the filtrate is concentrated. The residue is treated with EtOAc and filtered. The filtrate is washed with saturated aqueous solutions of NaHCO₃ and NaCl, dried over Na₂SO₄, filtered, and concentrated. The crude product is purified by flash chromatography (silica gel 60, 230–400 mesh, 4% methanol in chloroform) to afford 10.75 g of the title compound as a white foam; MS(CI), M+1=410.

Step 4: Preparation of Trp-NHOBn((S)-α-amino-N-(phenylmethoxy)-1H-indole-3-propanamide)

To a solution of Boc-Trp-NHOBn (3.48 g, 8.5 mmol) in dichloromethane (35 mL), is added portionwise trifluoroacetic acid (35 mL, 0.45 mol) at 0° C. with vigorous stirring. After addition of acid is complete the reaction mixture is stirred at room temperature for 1 hour and concentrated. The residue is taken up in EtOAc (50 mL) and the organic layer is cautiously washed with saturated aqueous NaHCO₃ until neutral. The organic layer is washed with saturated aqueous NaCl, dried over Na₂SO₄, and concentrated to afford 2.37 g of the title compound as a light yellow foam; MS(CI), M+1=310.

Step 5: Preparation of Trp-NHOBn.HCl((S)-α-amino-N-(phenylmethoxy)-1H-indole-3-propanamide, hydrochloride)

Hydrogen chloride gas is bubbled into a solution of BOC Trp-NHOBn (2.04 g, 5.0 mmol) in chloroform (100 mL) for 5 minutes at room temperature. The solution is stirred for 1 hour and concentrated to give 1.73 g of the title compound as an off-white solid; MS(CI), M+1=310.

Step 6: Preparation of Boc-Ile-Ile-Trp-NH-OBn(N-[1,1-dimethylethoxy)carbonyl]-L-isoleucyl-L-isoleucyl-N-(phenylmethoxy)-L-tryptophanamide)

A solution of Boc-Ile-Ile (2.65 g, 7.7 mol) with Trp-NHOBn (2.37 g, 7.7 mmol), and HOBt (1.25 g, 9.2 mmol) in DMF (50 mL) is treated with N-methyl-piperidine (1.10 mL), 9.2 mmol) followed by EDAC.HCl (1.76 g, 9.2 mmol) at 0° C. The reaction mixture is kept cold for 2 to 3 hours and stirred at room temperature for 15 hours. The solution is concentrated and the residue is partitioned between EtOAc and water. The bilayer is stirred at 0° C. for 2 hours. The precipitate is filtered and washed with water, diethyl ether, and a small amount of chloroform to afford 2.08 g of the title compound; MS fast atom bombardment (FAB), M+1=636.

EXAMPLE 2

Boc-Ile-Ile-Trp-NHOH(N-[(1,1-dimethylethoxy)carbonyl]-L-isoleucyl-L-isoleucyl-N-hydroxy-L-tryptophanamide)

A suspension of Boc-Ile-Ile-Trp NHOBn (Example 1) (0.76 g, 1.2 mmol) and Pd/BaSO₄ (5%, 0.60 g) in methanol (75 mL) is hydrogenated (53.4 psi) for 23 hours. TLC (SiO₂; CHCl₃:MeOH, 9:1) shows complete reaction of starting material. The reaction mixture is filtered through celite and the filtrate is concentrated. The crude product is purified by flash chromatography (silica gel 60, 230–400 mesh, chloroform:methanol 9:1) to afford 0.55 g of the title compound as a light orange, amorphous solid; MS(FAB), M+Na=568.

In a process analogous to Examples 1 and 2 using appropriate starting materials, the corresponding compounds of Formula I are prepared as follows:

EXAMPLE 3

Synthesis of Boc-Ile-Ile-D-Trp-NHOH(N-[(1,1-dimethyl-ethoxy) carbonyl]-L-isoleucyl-L-isoleuyl-N-hydroxy-D-tryptophanamide); MS(CI), M - CONHOH=485.

EXAMPLE 4

Synthesis of Boc-Ile-Trp-NHOH(N-[(1,1-dimethyl-ethoxy) carbonyl]-L-isoleucyl-N-hydroxy-L-tryptophanamide); MS(CI), M - CONHOH=372.

EXAMPLE 5

Ile-Ile-Trp-NHOBn(L-isoleucyl-L-isoleucyl-N-(phenylmethoxy-L-tryptophanamide)

To a suspension of Boc-Ile-Ile-Trp-NHOBn (Example 1) (1.50 g, 2.4 mmol) in dichloromethane (20 mL) is added portionwise trifluoroacetic acid (20 mL, 0.26 mol) at 0° C. with vigorous stirring. After addition is complete the reaction mixture is stirred at room temperature for 1 hour and concentrated. The residue is mixed with EtOAc and the organic layer is washed with saturated aqueous NaHCO₃. Upon neutralization of the excess acid, the product begins to precipitate in the organic layer. The organic suspension is diluted with diethyl ether and chilled at 0° C. for 1 hour. The title compound, 1.15 g, is collected as a light orange, amorphous solid; MS(CI), M+1=536.

EXAMPLE 6

Ile-Ile-Trp-NHOH(L-isoleucyl-L--isoleucyl-N-hydroxy-L-tryptophanamide, monohydrochloride)

Hydrogen chloride gas is bubbled into a partial suspension of N-[(1,1-dimethylethoxy) carbonyl]-L-isoleucyl-L-isoleucyl-N-hydroxy-L-tryptophanamide (Example 2) (200 mg, 3.67×10⁻⁴ mol) in chloroform (60 mL) for 5 minutes at room temperature. Upon the introduction of gas, all solid goes into solution and throughout the bubbling period a precipitate forms. After 1 hour the solution is concentrated to give 140 mg of the title compound as a pinkish-white amorphous solid; MS(FAB), M+1=446.2.

EXAMPLE 7

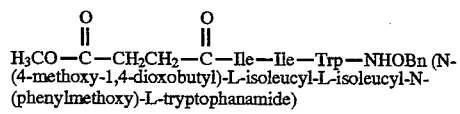
H₃CO—C(=O)—CH₂CH₂—C(=O)—Ile—Ile—Trp—NHOBn (N-(4-methoxy-1,4-dioxobutyl)-L-isoleucyl-L-isoleucyl-N-(phenylmethoxy)-L-tryptophanamide)

A solution of monomethyl succinate (0.32 g, 2.4 mmol) with Ile-Ile-Trp-NHOBn (Example 5) (1.15 g, 2.1 mmol), and HOBt (0.39 g, 2.9 mmol) in DMF (15 mL) is treated with N-methylpiperidine (0.35 mL, 2.9 mmol), followed by EDAC.HCl (0.55 g, 2.9 mmol) at 0° C. The reaction mixture is kept cold for 2 to 3 hours and stirred at room temperature for 14 hours. The reaction mixture is concentrated and the residue partitioned between EtOAc and water. After stirring for 30 minutes the product precipitates as a light yellow, amorphous solid which is washed with water and EtOAc and on filtration affords 0.87 g of the title compound; MS(FAB), M+1=650.

EXAMPLE 8

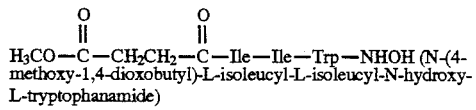
H₃CO—C—CH₂CH₂—C—Ile—Ile—Trp—NHOH (N-(4-methoxy-1,4-dioxobutyl)-L-isoleucyl-L-isoleucyl-N-hydroxy-L-tryptophanamide)

A solution of N-(4-methoxy-1,4-dioxobutyl)-L-isoleucyl-L-isoleucyl-N-(phenylmethoxy)-L-tryptophanamide (Example 7) (0.87 g, 1.3 mmol) and Pd/BaSO₄ catalyst (5%, 0.10 g) in MeOH (75 mL) is hydrogenated for 19 hours (52.6 psi). A precipitate forms during the course of the reaction and is dissolved upon addition of DMF. TLC (SiO₂, chloroform:MeOH 9:1) shows complete reaction of starting material. The catalyst is filtered using celite and the filtrate is concentrated. The residue is taken up in boiling MeOH and is refrigerated for 24 hours to precipitate 250 mg of the title compound; MS(FAB), M+Na=536.4.

EXAMPLE 9

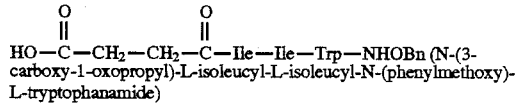
HO—C—CH₂—CH₂—C—Ile—Ile—Trp—NHOBn (N-(3-carboxy-1-oxopropyl)-L-isoleucyl-L-isoleucyl-N-(phenylmethoxy)-L-tryptophanamide)

A suspension of methyl ester

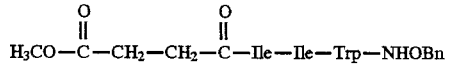
H₃CO—C—CH₂—CH₂—C—Ile—Ile—Trp—NHOBn (Example 7) (0.59 g, 9.08×10⁻⁴ mol). in methanol (10 mL) is treated with aqueous 1N NaOH (1.0 mL, 1.0×10⁻⁴ mol). The resulting solution is stirred at room temperature for 6 days after which time an additional amount of aqueous 1N NaOH (1.0 mL, 1.0×10⁻⁴ mol) is added and stirring continued for another 22 hours. The reaction mixture is concentrated and the residue is dissolved in water. The aqueous layer is extracted with EtOAc and the organic layer is discarded. The aqueous layer is filtered through celite and acidified to pH=2 with aqueous 1N HCl. The free acid precipitates as a gel and is washed with water and EtOAc and upon collection affords 0.41 g of the title compound; MS (FAB), M+1=636.4.

EXAMPLE 10

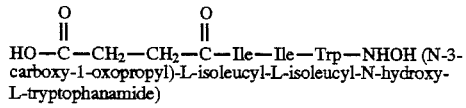
HO—C—CH₂—CH₂—C—Ile—Ile—Trp—NHOH (N-3-carboxy-1-oxopropyl)-L-isoleucyl-L-isoleucyl-N-hydroxy-L-tryptophanamide)

A suspension of

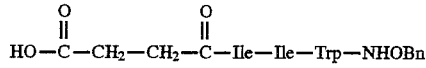
HO—C—CH₂—CH₂—C—Ile—Ile—Trp—NHOBn (Example 9) (0.32 g, 5.03×10⁻⁴ mol) and Pd/BaSO₄ (5%, 0.10 g) in methanol (75 mL) is hydrogenated (50.8 psi) for 18 hours. TLC (SiO₂; CHCl₃: MeOH, 9:1) shows complete reaction of starting material. The reaction mixture is filtered through celite and the filtrate is concentrated. The solid residue is suspended in hot, HPLC grade water and methanol is added dropwise until all remaining solids went into solution. The solution is filtered hot and the hydroxamate precipitates upon cooling. The light orange solid is collected and washed with HPLC grade water to afford 0.19 g of the title compound; MS(FAB), M+Na=568.4.

EXAMPLE 11

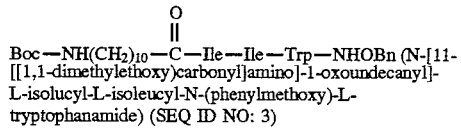
Boc—NH(CH₂)₁₀—C—Ile—Ile—Trp—NHOBn (N-[11-[[(1,1-dimethylethoxy)carbonyl]amino]-1-oxoundecanyl]-L-isolucyl-L-isoleucyl-N-(phenylmethoxy)-L-tryptophanamide) (SEQ ID NO: 3)

Step 1: Preparation of

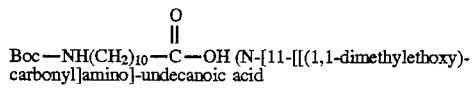
Boc—NH(CH₂)₁₀—C—OH (N-[11-[[(1,1-dimethylethoxy)carbonyl]amino]-undecanoic acid A suspension of 11-aminoundecanoic acid (7.0 g, 0.035 mol), di-tert-butyl dicarbonate (8.45 g, 0.039 mol), and triethylamine (5.30 mL, 0.039 mol) in methanol (100 mL) is stirred at room temperature under nitrogen atmosphere for 20 hours. The resultant solution is concentrated and the residue is partitioned between water and diethyl ether. The aqueous layer is washed with diethyl ether and acidified to pH=2 with aqueous 1N HCl. The acid layer is extracted with EtOAc and the organic extract dried over MgSO₄, filtered, and concentrated to afford 7.59 g of the title compound as a white, amorphous solid; MS(CI), M+1=302.

Step 2: Preparation of Ile-Ile-OCH₃.HCl(methyl-N-L-isoleucyl-L-isoleucine, monohydrochloride)

Hydrogen chloride gas is bubbled into a solution of Boc-Ile-Ile-OCH₃ (Example 1, Step 1) (3.0 g, 8.4 mmol) in chloroform (100 mL) for 5 minutes at room temperature. After stirring for an additional 1 hour the solution is concentrated to afford 2.48 g of the title compound as a white, amorphous solid; MS(CI), M+1=259.

Step 3: Preparation of

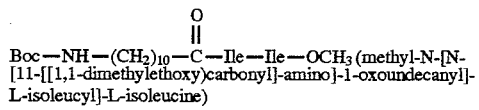
Boc—NH—(CH₂)₁₀—C—Ile—Ile—OCH₃ (methyl-N-[N-[11-[[1,1-dimethylethoxy)carbonyl]-amino]-1-oxoundecanyl]-L-isoleucyl]-L-isoleucine)

A mixture of

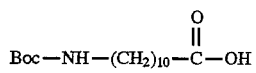
Boc—NH—(CH₂)₁₀—C—OH (2.68 g, 8.9 mmol), Ile-Ile-OCH₃.HCl (2.62 g, 8.9 mmol), and HOBt (1.44 g, 10.7 mmol) in DMF (50 mL) is treated with triethylamine (3.02 mL, 2.19 g, 22.2 mmol) followed by DCC (2.02 g, 9.8 mmol) at 0° C. The reaction mixture is kept cold for 2 to 3 hours and allowed to warm up to room temperature over a period of 15 hours. The resulting suspension is filtered and the filtrate is concentrated. The residue is mixed with ethyl acetate and the solution is filtered. The filtrate is washed with saturated aqueous solutions of NaHCO₃ and NaCl, dried over Na₂SO₄, filtered, and concentrated. The crude product is purified by flash chromatography (silica gel 60, 230–400 mesh, hexane:EtOAc, 7:3 to 3:2) to give 3.68 g of the title compound as a clear, viscous foil; MS(CI), M=541.

Step 4: Preparation of

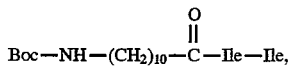

sodium salt (N-[11-[[(1,1-dimethylethoxy)carbonyl]-amino]1-oxoundecanyl]-L-isoleucyl]-L-isoleucine, monosodium salt)

A solution of

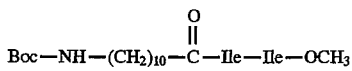

(3.58 g, 6.6 mmol) in methanol (40 mL) is treated portionwise with aqueous 1N NaOH (7.3 mL, 7.3 mmol). After addition is complete, the reaction mixture is stirred at room temperature for 5 days. An insoluble residue is removed by filtration and the filtrate is concentrated to afford 3.70 g of the title compound as a white foam.

Step 5: Preparation of

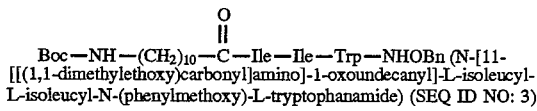

A solution of

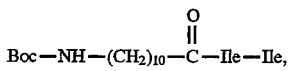

sodium salt (3.70 g, 6.7 mmol), Trp-NHOBn (Example 1, Step 4) (2.27 g, 7.3 mmol), and HOBt (1.08 g, 8.0 mmol) in DMF (60 mL) is treated with N-methylpiperidine (1.62 mL, 13.4 mmol) and EDAC-HCl (1.54 g, 8.0 mmol) at 0° C. The reaction mixture is kept cold for 2 to 3 hours and allowed to warm to room temperature over 19 hours. The reaction mixture is concentrated and the residue is partitioned between EtOAc and saturated aqueous NaHCO₃. The bilayer is vigorously stirred for 1 hour at 0° C., and the white precipitate which forms, is filtered and washed with water, EtOAc, and a small amount of methanol to afford 4.70 g of the title compound; MS(FAB), M+Na=841.7.

EXAMPLE 12

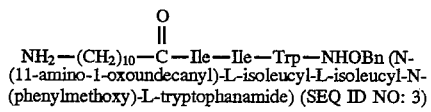

To a suspension of

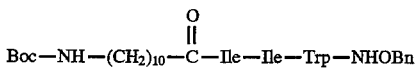

(Example 11) (SEQ ID NO: 3) (1.14 g, 1.4 mmol) in dichloromethane (50 mL) is added dropwise trifluoroacetic acid (30 mL, 0.39 mol) at 0° C. After the addition of acid, a homogeneous solution is obtained. The reaction mixture is stirred at room temperature for 1 hour and concentrated. The residue is partitioned between EtOAc and saturated aqueous NaHCO₃. A white solid (1.27 g) precipitates and is suspended in boiling water. Methanol is added dropwise until homogeneous. The solution is filtered hot and upon cooling 0.42 g of the title compound precipitates as a white, amorphous solid; MS(FAB), M+1=719.6.

EXAMPLE 13

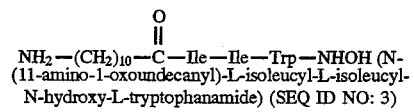

A suspension of

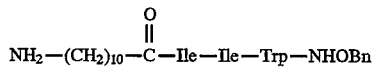

(Example 12) (SEQ ID NO: 3) (200 mg, 0.28 mmol) and Pd/BaSO₄ (5%, 0.1 g) in methanol (75 mL) is hydrogenated (52.3 psi) for 15 hours. TLC (SiO₂; CHCl₃: MeOH, 9:1) shows complete loss of starting material. The reaction mixture is filtered through celite and the filtrate is concentrated to give the title compound as a white solid (122 mg). The catalyst is suspended in boiling methanol and filtered through celite. The filtrate is concentrated to a solid (35 mg) which had identical analytical data with the initial product isolated; MS(FAB), M+1=629.

EXAMPLE 14

Boc-Ile-Trp-NHOBn(N-[(1,1-dimethylethoxy)carbonyl]-L-isoleucyl-N-(phenylmethoxy)-L-tryptophanamide)

A solution of Boc-Ile (0.74 g, 3.2 mmol) and Trp-NHOBn (Example 1, Step 4) (0.98 g, 3.2 mmol) in DMF (20 mL) cooled to 0° C. is treated with HOBt (0.51 g, 3.8 mmol), followed by DCC (0.72 g, 3.5 mmol). The reaction mixture is kept cold for 2 to 3 hours and stirred at room temperature for a total of 13 hours. The reaction mixture is filtered and the filtrate is concentrated. The residue is treated with EtOAc and the solution is filtered. The filtrate is washed with saturated aqueous solutions of NaHCO₃ and NaCl, dried over Na₂SO₄, and concentrated. The crude product is purified by flash chromatography (silica gel 60, 230–400 mesh, 4% methanol in chloroform) to give 0.76 g of the title compound as a yellow foam; MS(CI), M+1=523.

EXAMPLE 15

Boc-Trp(For)OBn(phenylmethyl-N-[(1,1-dimethylethoxy)-carbonyl]-1-formyl-L-tryptophan)

To a solution of N-α-Boc-N-indoleformyltryptophan (3.99 g, 0.0126 mmol), benzyl alcohol (1.33 mL, 0.0129 mmol), and 4-dimethylaminopyridine (DMAP, 0.30 g, 2.6 mmol) in methylene chloride (70 mL) is added DCC (2.54 g, 0.0126 mol). The reaction mixture is stirred under nitrogen at room temperature for 17 hours after which time the precipitated urea is filtered and the filtrate is concentrated. The residue is taken up in EtOAc and refiltered. The filtrate is washed with saturated aqueous solutions of NaHCO₃ and NaCl, dried over MgSO₄, filtered, and concentrated. The crude product is purified by flash chromatography (silica gel 60, 230–400 mesh, 7:3 hexane:EtOAc) to give 4.25 g of the title compound as a white, crystalline solid which is washed with hexane upon collection; MS(CI), M+1=422.

EXAMPLE 16

Trp(For)OBn(phenylmethyl-1-formyl-L-tryptophan)

The Boc group of Boc-Trp(For)OBn (6.60 g, 0.016 mol) is removed using the procedure described in Example 1, Step 4, to give 4.80 g of the title compound.

EXAMPLE 17

Boc-Ile-Ile-Trp(For)QBn(phenylmethyl-N-[N-[N-[(1,1-dimethylethoxy)carbonyl]-L-isoleucyl]-L-isoleucyl]-1-formyl-L-tryptophan)

A solution of Boc-Ile-Ile (4.64 g, 0.013 mol), Trp(For)OBn (Example 14) (4.34 g, 0.013 mol), and HOBt (2.23 g, 0.016 mol) in DMF (80 mL) cooled to 0° C. is treated with DCC (2.99 g, 0.014 mol). The reaction mixture is kept cold for 2 to 3 hours and stirred at room temperature for 16 hours. The reaction mixture is filtered and the filtrate is concentrated. The residue was taken up in warm EtOAc and the organic layer is washed with saturated aqueous solutions of $NaHCO_3$ and NaCl, dried over $MgSO_4$, filtered, and concentrated (upon cooling of the organic layer a small amount of product precipitation is observed). The crude product is purified by flash chromatography (silica gel 60, 230–400 mesh, 7:3 hexane:EtOAc to 3:2 hexane:EtOAc) to give 3.92 g of the title compound as a white solid; MS(CI), M+1=649.

EXAMPLE 18

Boc-Ile-Ile-Trp(For)OH(N-[N-[N-[(1,1-dimethylethoxy)-carbonyl]-L-isoleucyl]-L-isoleucyl]-1-formyl-L-tryptophan)

A solution of Boc-Ile-Ile-Trp(For)OBn (Example 17) (1.50 g, 2.3 mmol) and Pd/C (20%, 1.0 g) in methanol (100 mL) is hydrogenated (50 psi) for 2 hours. TLC ($SiO_2$; hexane:EtOAc 1:1) shows complete loss of starting material. The reaction mixture is filtered through celite and the filtrate is concentrated to give 1.28 g of the title compound; MS (CI), M+1=559.

EXAMPLE 19

Boc-Ile-Ile-Trp(For)NHOBn(N-[(1,1-dimethylethoxy)-carbonyl]-L-isoleucyl-L-isoleucyl-1-formyl-N-(phenyl-methoxy)-L-tryphophanamide)

Boc-Ile-Ile-Trp (For) OH (Example 18) (1.27 g, 2.3 mmol) is coupled with O-benzylhydroxylamine hydrochloride (0.37 g, 2.3 mmol) using the procedure described in Example 1, Step 3. The crude product is purified by flash chromatography (silica gel 60, 230–400 mesh, 4% methanol in chloroform) to give 0.99 g of the title compound as an orange, amorphous solid; MS(FAB) M+1=664.

EXAMPLE 20

Ile-Ile-Trp(For)NHOBn(L-isoleucyl-L-isoleucyl-1-formyl-N-(phenylmethoxy)-L-tryptophanamide)

The Boc group of Boc-Ile-Ile-Trp(For)NHOBn (Example 19) (0.95 g, 1.5 mmol) is removed using the procedure described in Example 10 to give 0.64 g of the title compound as a white solid.

EXAMPLE 21

Boc-Asp(OBn)-Ile-Ile-Trp(For)-NHOBn (phenylmethyl-N-[(1,1-dimethylethoxy)carbonyl]-L-α-aspartyl-L-isoleucyl-L-isoleucyl-1-formyl-N-(phenylmethoxy)-L-tryptophanamide) (SEQ ID NO: 4)

Ile-Ile-Trp(For)NHOBn (Example 20) (0.64 g, 1.1 mmol) is coupled with Boc-aspartic acid-β-benzyl ester (0.36 g, 1.1 mmol) according to the procedure described in Example 15. The crude product is purified by flash chromatography (silica gel 60, 230–400 mesh, 3% methanol in chloroform) to give 0.69 g of the title compound as an orange foam; MS (FAB), M+Na+H=893.

EXAMPLE 22

Boc-Asp-Ile-Ile-Trp(For)-NHOH (N-[(1,1-dimethylethoxy)-carbonyl]-L-α-aspartyl-L-isoleucyl-n-isoleucyl-1-formyl-N-hydroxy-n-tryptophanamide) (SEQ ID NO: 4)

Boc-Asp (OBn)-Ile-Ile-Trp(For)NHOBn (Example 21) (SEQ ID NO: 4) (0.65 g, 7.5×10$^{-4}$ mmol) is hydrogenated according to the procedure described in Example 8 to give 0.51 g of the title compound as a light orange foam; MS (FAB), M+Na+$H_2$=713.

---

We claim:

1. A compound of Formula I $$R-AA^1-AA^2-AA^3-AA^4-AA^5-AA^6-N(R^1)-OR^2 \text{ (SEQ ID NO: 2)} \quad I$$

wherein R is hydrogen, $$R^3-[NH(CH_2)_n-\underset{\underset{}{\overset{O}{\|}}}{C}]_m-$$

wherein $R^3$ is hydrogen, tert-butyloxycarbonyl, carbobenzyloxy, 9-fluorenylmethyloxycarbonyl, benzyl, acetyl, or phthaloyl, n is an integer of one to ten, m is zero or an integer of one or

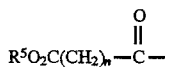

wherein $R^5$ is hydrogen or alkyl, and n is as defined above;

$AA^1$ and $AA^2$ are absent;

$AA^3$ is Asp,
 Asn,
 Glu,
 Gln,
 Asp (Ot—Bu),
 Asp (OMe),
 Glu (Ot—Bu), or
 Glu (OMe), or $AA^3$ is absent;

$AA^4$ and $AA^5$ are both independently
 Leu,
 Ile,
 Nle,
 Val,
 Nva,
 Ala,
 Chx,
 Gly,
 Alg,
 Cprl, or
 Pgy;

$AA^6$ is Trp,
 Trp(For),
 Trp (Me),
 His,
 Phe,
 Tyr,
 Tyr(OMe),
 Tyr(Ot—Bu),
 1-Nal,
 2-Nal,
 Bta,
 Bfa,
 Pyr, or
 HomoPhe;

$R^1$ and $R^2$ are hydrogen; or a pharmaceutically acceptable salt thereof.

2. A compound according to claim 1 selected from the group consisting of
 Ile-Ile-Trp-NHOH;
 Boc-Ile-Ile-Trp-NHOH;

wherein R is hydrogen,
 methyl,
 ethyl, or
 t-butyl, and
 n is an integer of one to ten;

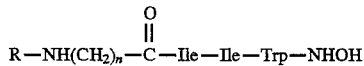  (SEQ ID NO: 3)

wherein R is hydrogen,
 Boc, or
 CBZ, and
 n is an integer of one to ten;

Asp-Ile-Ile-Trp-NHOH (SEQ ID NO: 4);

Boc-Asp-Ile-Ile-Trp-NHOH (SEQ ID NO: 4);

  (SEQ ID NO: 4)

wherein R is hydrogen,
 methyl,
 ethyl, or
 t-butyl, and
 n is an integer of one to ten;

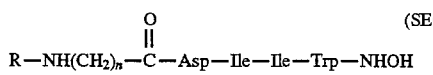  (SEQ ID NO: 5)

wherein R is hydrogen,
 Boc, or
 CBZ, and
 n is an integer of one to ten;

Ile-Ile-Phe-NHOH;
Boc-Ile-Ile-Phe-NHOH;

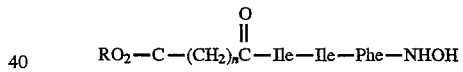

wherein R is hydrogen,
 methyl,
 ethyl, or
 t-butyl, and
 n is an integer of one to ten;

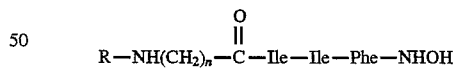  (SEQ ID NO: 10)

wherein R is hydrogen,
 BOC, or
 CBZ, and
 n is an integer of one to ten;

Ile-Ile-1-Nal-NHOH;
Boc-Ile-Ile-1-Nal-NHOH;

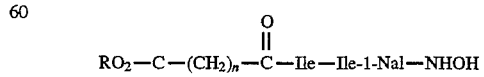

wherein R is hydrogen,
 methyl,
 ethyl, or t-butyl, and
n is an integer of one to ten;

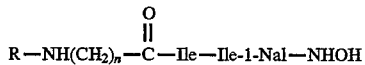 (SEQ ID NO: 11)

wherein R is hydrogen,
Boc, or
CBZ, and
n is an integer of one to ten;
Ile-Ile-2-Nal-NHOH;
Boc-Ile-Ile-2-Nal-NHOH;

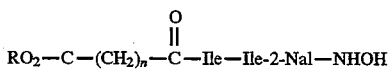

wherein R is hydrogen,
methyl,
ethyl, or
t-butyl, and
n is an integer of one to ten;

 (SEQ ID NO: 11)

wherein R is hydrogen,
Boc, or
CBZ, and
n is an integer of one to ten;
Ile-Ile-Bta-NHOH;
Boc-Ile-Ile-Bta-NHOH;

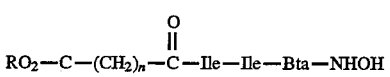

wherein R is hydrogen,
methyl,
ethyl, or
t-butyl, and
n is an integer of one to ten;

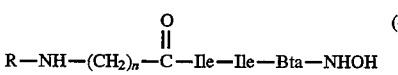 (SEQ ID NO: 11)

wherein R is hydrogen,
Boc, or
CBZ, and
n is an integer of one to ten;
Ile-Ile-Bfa-NHOH;
Boc-Ile-Ile-Bfa-NHOH;

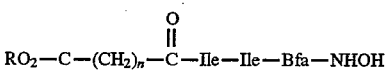

wherein R is hydrogen,
methyl,
ethyl, or
t-butyl, and
n is an integer of one to ten;

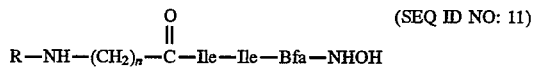 (SEQ ID NO: 11)

wherein R is hydrogen,
Boc, or
CBZ, and
n is an integer of one to ten;
Asp-Ile-Ile-Phe-NHOH (SEQ ID NO: 12);
Boc-Asp-Ile-Ile-Phe-NHOH (SEQ ID NO: 12);

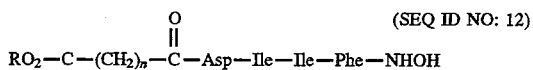 (SEQ ID NO: 12)

wherein R is hydrogen,
methyl,
ethyl, or
t-butyl, and
n is an integer of one to ten;

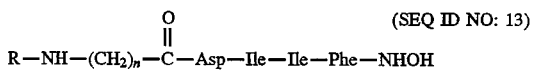 (SEQ ID NO: 13)

wherein R is hydrogen,
Boc, or
CBZ, and
n is an integer of one to ten;
Asp-Ile-Ile-1-Nal-NHOH (SEQ ID NO: 14);
Boc-Asp-Ile-Ile-1-Nal-NHOH (SEQ ID NO: 14);

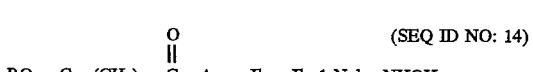 (SEQ ID NO: 14)

wherein R is hydrogen,
Boc, or
CBZ, and
n is an integer of one to ten;

 (SEQ ID NO: 15)

wherein R is hydrogen,
Boc, or
CBZ, and
n is an integer of one to ten;
Asp-Ile-Ile-2-Nal-NHOH (SEQ ID NO: 14);
Boc-Asp-Ile-Ile-2-Nal-NHOH (SEQ ID NO: 14);

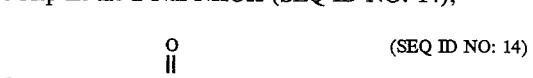 (SEQ ID NO: 14)

wherein R is hydrogen,
Boc, or
CBZ, and
n is an integer of one to ten;

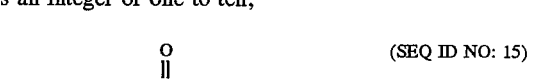 (SEQ ID NO: 15)

wherein R is hydrogen,

Boc, or

CBZ, and n is an integer of one to ten.

3. A method of treating hypertension comprising administering to a mammal suffering therefrom a therapeutically effective amount of a compound according to claim 1 in unit dosage form.

4. A method of treating congestive heart failure and myocardial infarction comprising administering to a mammal suffering therefrom a therapeutically effective amount of a compound according to claim 1 in unit dosage form.

5. A method of treating asthma comprising administering to a mammal suffering therefrom a therapeutically effective amount of a compound according to claim 1 in unit dosage form.

6. A method of treating acute renal failure comprising administering to a mammal suffering therefrom a therapeutically effective amount of a compound according to claim 1 in unit dosage form.

7. A method of treating pulmonary hypertension comprising administering to a mammal suffering therefrom a therapeutically effective amount of a compound according to claim 1 in unit dosage form.

8. A method of treating cerebral vasospasm comprising administering to a mammal suffering therefrom a therapeutically effective amount of a compound according to claim 1 in unit dosage form.

9. A pharmaceutical composition comprising a therapeutically effective amount of a compound according to claim 7 in admixture with a pharmaceutically acceptable excipient, diluent, or carrier.

10. A pharmaceutical composition adapted for administration as an inhibitor of endothelin converting enzyme, as an antihypertensive agent, as an agent for treating congestive heart failure and myocardial infarction, as an agent for treating subarachnoid hemorrhage, as an agent for treating asthma, as an agent for treating acute renal failure, as an agent for treating pulmonary hypertension, as or as an agent for treating cerebral vasospasm comprising a therapeutically effective amount of a compound according to claim 1 in admixture with a pharmaceutically acceptable excipient, diluent, or carrier.

11. A mixture of two or more compounds according to claim 1, wherein in the said mixture the stereochemistry of any of $AA^3$, $AA^4$, $AA^5$ and $AA^6$ is L, D or DL.

* * * * *

UNITED STATES PATENT AND TRADEMARK OFFICE
CERTIFICATE OF CORRECTION

PATENT NO. : 5,663,296

DATED : September 2, 1997

INVENTOR(S) : Annette Marian Doherty, Brian Edward Kornberg, Sham Nikam

It is certified that error appears in the above-indentified patent and that said Letters Patent is hereby corrected as shown below:

Column 45, line 36, delete "Cprl" and insert --Cpn--.

Column 46, line 30, should read --wherein R is hydrogen,
              Boc, or
              CBZ, and
        n is an integer of one to ten;
   Leu-Asp-Ile-Ile-Trp-NHOH   (SEQ ID NO:  6);
   Boc-Leu-Asp-Ile-Ile-Trp-NHOH (SEQ ID NO:  6);

$$RO_2\text{-C-}(CH_2)_n\text{-}\overset{\overset{O}{\|}}{C}\text{-Leu-Asp-Ile-Ile-Trp-NHOH}$$ (SEQ ID NO: 6)

wherein R is hydrogen,
           methyl,
           ethyl, or
           t-butyl, and
        n is an integer of one to ten;

$$R\text{-NH-}(CH_2)\text{-}_n\text{-}\overset{\overset{O}{\|}}{C}\text{-Leu-Asp-Ile-Ile-Trp-NHOH}$$ (SEQ ID NO: 7)

wherein R is hydrogen,
           Boc, or
           CBZ, and
        n is an integer of one to ten;
   His-Leu-Asp-Ile-Ile-Trp-NHOH  (SEQ ID NO:  8);
   Boc-His-Leu-Asp-Ile-Ile-Trp-NHOH   (SEQ ID NO:  8);

UNITED STATES PATENT AND TRADEMARK OFFICE
CERTIFICATE OF CORRECTION

PATENT NO. : 5,663,296
DATED : September 2, 1997
INVENTOR(S) : Annette Marian Doherty, Brian Edward Kornberg, Sham Nikam It is certified that error appears in the above-indentified patent and that said Letters Patent is hereby corrected as shown below:

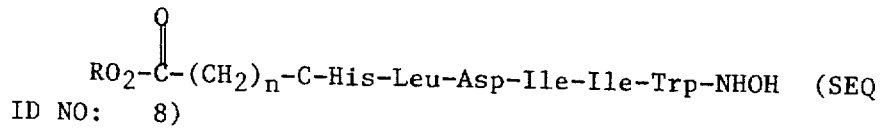  (SEQ ID NO: 8)

wherein R is hydrogen,
                methyl,
                ethyl, or
                t-butyl, and
        n is an integer of one to ten;

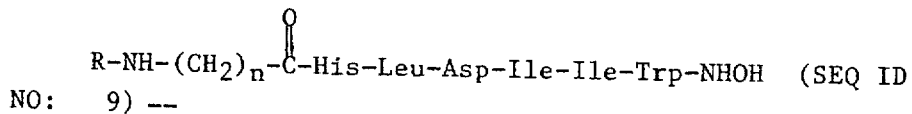 (SEQ ID NO: 9) --

Column 50, in Claim 10, line 15, after the words 'hypertension, as', insert --an agent for treating cerebral ischemia,--.

Signed and Sealed this

Twenty-sixth Day of October, 1999

*Attest:*

*Attesting Officer*

Q. TODD DICKINSON

*Acting Commissioner of Patents and Trademarks*